United States Patent
Steele

(10) Patent No.: US 9,610,245 B2
(45) Date of Patent: Apr. 4, 2017

(54) OPHTHALMIC COMPOSITION

(75) Inventor: Fraser Steele, Horsham (GB)

(73) Assignee: Drug Delivery Solutions Limited, Leatherhead, Surrey (GB)

( * ) Notice: Subject to any disclaimer, the term of this patent is extended or adjusted under 35 U.S.C. 154(b) by 0 days.

(21) Appl. No.: 14/003,871

(22) PCT Filed: Mar. 14, 2012

(86) PCT No.: PCT/EP2012/054498
§ 371 (c)(1),
(2), (4) Date: Sep. 9, 2013

(87) PCT Pub. No.: WO2012/123515
PCT Pub. Date: Sep. 20, 2012

(65) Prior Publication Data
US 2013/0345150 A1  Dec. 26, 2013

(30) Foreign Application Priority Data

Mar. 14, 2011 (EP) .................................... 11158099

(51) Int. Cl.
| | | |
|---|---|---|
| *A61K 9/10* | (2006.01) | |
| *A61K 38/13* | (2006.01) | |
| *A61K 9/00* | (2006.01) | |
| *A61K 31/573* | (2006.01) | |
| *A61K 31/59* | (2006.01) | |

(52) U.S. Cl.
CPC .............. *A61K 9/0048* (2013.01); *A61K 9/10* (2013.01); *A61K 31/573* (2013.01); *A61K 31/59* (2013.01)

(58) Field of Classification Search
CPC .... A61K 9/0048; A61K 31/573; A61K 31/59; A61K 9/10
See application file for complete search history.

(56) References Cited

U.S. PATENT DOCUMENTS

| | | |
|---|---|---|
| 4,486,333 A | 12/1984 | Sebba |
| 4,533,546 A | 8/1985 | Kishi et al. |
| 4,871,723 A | 10/1989 | Makino et al. |
| 4,900,552 A | 2/1990 | Sanvordeker et al. |
| 4,936,933 A | 6/1990 | Yabsley et al. |
| 4,944,938 A | 7/1990 | Potini |
| 4,999,198 A | 3/1991 | Barnett et al. |
| 5,474,979 A | 12/1995 | Ding et al. |
| 5,573,757 A | 11/1996 | Riess et al. |
| 5,645,856 A | 7/1997 | Lacy et al. |
| 5,660,858 A | 8/1997 | Parikh et al. |
| 5,763,426 A | 6/1998 | Hansen et al. |
| 5,840,881 A | 11/1998 | Uda et al. |
| 5,952,383 A | 9/1999 | Metziger et al. |
| 5,955,097 A | 9/1999 | Tapolsky et al. |
| 5,990,100 A | 11/1999 | Rosenberg et al. |
| 6,096,338 A | 8/2000 | Lacy et al. |
| 6,165,479 A | 12/2000 | Wheeler |
| 6,200,581 B1 | 3/2001 | Lin et al. |
| 6,238,678 B1 | 5/2001 | Oblong et al. |
| 6,538,039 B2 | 3/2003 | Laurent |
| 6,562,370 B2 | 5/2003 | Luo et al. |
| 6,585,997 B2 | 7/2003 | Moro et al. |
| 6,599,527 B1 | 7/2003 | Leigh et al. |
| 6,753,013 B1 | 6/2004 | Didriksen et al. |
| 6,787,529 B2 | 9/2004 | Hoy et al. |
| 7,001,607 B1 | 2/2006 | Menz et al. |
| RE39,706 E | 6/2007 | Hansen et al. |
| 8,263,580 B2 | 9/2012 | Buchta et al. |
| 8,298,515 B2 | 10/2012 | Buchta et al. |
| 8,629,111 B2 | 1/2014 | Acheampong et al. |
| 8,629,128 B2 | 1/2014 | Buchta et al. |
| 8,633,162 B2 | 1/2014 | Acheampong et al. |
| 8,642,556 B2 | 2/2014 | Acheampong et al. |
| 8,648,008 B2 | 2/2014 | Misra et al. |
| 2005/0001643 A1 | 1/2005 | Yoshida et al. |
| 2005/0002546 A1 | 1/2005 | Florent et al. |
| 2005/0020546 A1 | 1/2005 | Laidlaw et al. |
| 2005/0026877 A1 | 2/2005 | Chen et al. |
| 2005/0082515 A1 | 4/2005 | Masuichi et al. |
| 2005/0147658 A1 | 7/2005 | Tapolsky et al. |
| 2005/0238676 A1 | 10/2005 | Gladman et al. |
| 2005/0281749 A1 | 12/2005 | Willcox et al. |
| 2005/0281750 A1 | 12/2005 | Willcox et al. |
| 2005/0281754 A1 | 12/2005 | Willcox et al. |
| 2005/0281755 A1 | 12/2005 | Zarif et al. |
| 2005/0281848 A1 | 12/2005 | Zanutto et al. |
| 2005/0281850 A1 | 12/2005 | Zanutto et al. |
| 2005/0282788 A1 | 12/2005 | Zanutto et al. |
| 2005/0282792 A1 | 12/2005 | Andres |
| 2006/0147383 A1 | 7/2006 | Mallard et al. |

(Continued)

FOREIGN PATENT DOCUMENTS

| | | |
|---|---|---|
| CN | 1351499 A | 5/2002 |
| CN | 1832731 A | 9/2006 |

(Continued)

OTHER PUBLICATIONS

Capric/Caprylic Triglyceride vs. Fractionated Coconut Oil, from http://chemicaloftheday.squarespace.com/qa/2015/2/8/capric-caprylic-triglyceride-vs-fractionated-coconut-oil.html, pp. 1-6, accessed Jun. 12, 2015.*
Gelatine, from http://www.gelita.com/solutions-and-products/gelatine-gelling-agent-numerous-applications, p. 1, accessed Jun. 13, 2015.*
Eyedrops Medical Definition, from http://www.merriam-webster.com/medical/eyedrops, p. 1, accessed Dec. 24, 2015.*
Rathore et al, An Insight into Ophthalmic Drug Delivery System, International Journal of Pharmaceutical Sciences and Drug Research, 2009, 1, pages 1-5.*
Patel et al, Ophthalmic Drug Delivery System—A Review, Der Pharmacia Lettre, 2010, 2, pp. 100-115, published on Feb. 4, 2010.*
PCT/EP2012/054498 International Search Report dated May 7, 2012.
Adams, "Vitamin D mythes, facts and statistics," Natural News, 2005, Abstract.
Ashcroft et al., "Systematic Review . . . Plaque Psoriasis" British Medical Journal, 320:963-967 (2000).

(Continued)

*Primary Examiner* — Julie Ha
*Assistant Examiner* — Li Ni Komatsu
(74) *Attorney, Agent, or Firm* — Merchant & Gould P.C.

(57) ABSTRACT

An ophthalmic composition comprising a polyaphron dispersion.

15 Claims, 1 Drawing Sheet

(56) References Cited

U.S. PATENT DOCUMENTS

| | | |
|---|---|---|
| 2006/0188576 A1 | 8/2006 | Takruri |
| 2006/0228408 A1 | 10/2006 | Charman et al. |
| 2006/0239947 A1 | 10/2006 | Dias et al. |
| 2006/0292080 A1 | 12/2006 | Abram et al. |
| 2007/0041910 A1 | 2/2007 | Pitre et al. |
| 2007/0048369 A1 | 3/2007 | Foreman et al. |
| 2007/0059346 A1 | 3/2007 | Maibach |
| 2007/0190088 A1 | 8/2007 | Childs et al. |
| 2007/0207192 A1 | 9/2007 | Holl et al. |
| 2008/0207570 A1 | 8/2008 | Segura-Orsni |
| 2008/0234239 A1 | 9/2008 | Wheeler et al. |
| 2008/0254105 A1 | 10/2008 | Tapolsky et al. |
| 2010/0062975 A1* | 3/2010 | Houck ............................ 514/11 |
| 2010/0279951 A1 | 11/2010 | Morgan et al. |
| 2013/0101525 A1 | 4/2013 | Buchta et al. |

FOREIGN PATENT DOCUMENTS

| | | | |
|---|---|---|---|
| EP | 0474517 A2 | 3/1992 | |
| EP | 0679154 A1 | 11/1995 | |
| EP | 0679392 A1 | 11/1995 | |
| EP | 0799620 A1 * | 10/1997 | ............ A61K 38/13 |
| EP | 0884995 A1 | 12/1998 | |
| EP | 1039893 A1 | 10/2000 | |
| EP | 1178808 A1 | 2/2002 | |
| EP | 1575542 B1 | 9/2005 | |
| EP | 1641463 A1 | 4/2006 | |
| EP | 1686972 A1 | 8/2006 | |
| EP | 1758586 A1 | 3/2007 | |
| EP | 1758587 A1 | 3/2007 | |
| EP | 1758588 A1 | 3/2007 | |
| EP | 1758589 A1 | 3/2007 | |
| EP | 1758591 A1 | 3/2007 | |
| EP | 1765356 A1 | 3/2007 | |
| EP | 1970047 A1 | 3/2007 | |
| EP | 1970048 A1 | 3/2007 | |
| EP | 1771180 A1 | 4/2007 | |
| EP | 1778185 A1 | 5/2007 | |
| EP | 1331927 B1 | 12/2007 | |
| EP | 1970047 A1 | 9/2008 | |
| EP | 1970048 A1 | 9/2008 | |
| EP | 1970049 A1 | 9/2008 | |
| JP | 62-135417 | 6/1987 | |
| JP | 2005-325140 A | 11/2005 | |
| RU | 2238734 C2 | 10/2004 | |
| RU | 2276177 C2 | 9/2010 | |
| WO | WO 95/31211 A1 | 11/1995 | |
| WO | WO 96/25923 A1 | 8/1996 | |
| WO | WO 96/00074 A1 | 10/1996 | |
| WO | WO 97/32559 A1 | 9/1997 | |
| WO | WO 99/55312 A1 | 11/1999 | |
| WO | WO 00/64450 A1 | 11/2000 | |
| WO | WO 01/62214 A1 | 8/2001 | |
| WO | WO 02/04570 A2 | 1/2002 | |
| WO | WO 02/34235 A1 | 5/2002 | |
| WO | WO 2004/041227 A1 | 5/2004 | |
| WO | WO 2005/001643 A2 | 1/2005 | |
| WO | WO 2005/011628 A2 | 2/2005 | |
| WO | WO 2005/011643 A1 | 2/2005 | |
| WO | WO 2005/016321 A1 | 2/2005 | |
| WO | WO2005011628 A2 | 2/2005 | |
| WO | WO 2005/061321 A2 | 7/2005 | |
| WO | WO 2005/082515 A2 | 9/2005 | |
| WO | WO 2006/050836 A2 | 5/2006 | |
| WO | WO 2006/111426 A1 | 10/2006 | |
| WO | WO 2008/110815 A1 | 9/2008 | |
| WO | WO2008110815 A1 | 9/2008 | |
| WO | WO 2009/001099 A2 | 12/2008 | |
| WO | WO2009001099 A2 | 12/2008 | |
| WO | WO 2009/007409 A2 | 1/2009 | |
| WO | WO 2009/071594 A1 | 6/2009 | |
| WO | WO 2010/120838 A1 | 10/2010 | |
| WO | WO 2010/124096 A1 | 10/2010 | |
| WO | WO2010120838 A1 | 10/2010 | |
| WO | WO 2010/141591 A1 | 12/2010 | |

OTHER PUBLICATIONS

Charakida et al., "Calcipotriol/betamethasone dipropionate for the treatment of psoriasis," Expert Opin. Pharmacother, 7(5):597-606 (2006).
Office Action for Chinese Patent Application No. 200880008496.X (with English translation) (11 pages).
EP 11158099.9 Search Report dated Sep. 20, 2011.
EP Application No. 1196067.0 Ryttov Declaration (4 pages).
EP Application No. 11196069.6 Response filed Aug. 8, 2013 (93 pages).
Farines et al., "Analysis of the triglycerides of some vegetable oils," Journal of Chemical Education, 65(5):464-466 (1988).
Final Report on the safety assessment of peanut (Arachis hypogaea) oil etc. International Journal of Toxicology, 20(2):65-77 (2001).
Guenther et al., "Efficacy and safety of a new combination of calcipotriol and betamethasone dipropionate (once or twice daily) compared to calcipotriol (twice daily) in the treatment of psoriasis vulgaris: a randomized, double-blind, vehicle-controlled clinical trial," British Journal of Dermatology, 147:316-323 (2002).
Kaufmann et al., "A New Calcipotriol/Betamethasone Dipropionate Formulation (DaivobetTM) is an Effective Once-Daily Treatment for Psoriasis vulgaris," Dermatology, 205:389-393 (2005).
Kim et al., "Lipolysis of Corn, peanut and randomized peanut oils," Lipids, 18(11):842-844 (1983).
Kragballe, "Treatment of psoriasis with calcipotriol and other vitamin D analogues," Journal of the American Academy of Dermatology, Dec. 1992, vol. 27, Issue 6, part 1 (Abstract only).
Kragballe et al., "Efficacy of once-daily treatment regimens wit calcipotriol/betamethasone dipropionate ointment and calcipotriol ointment in psoriasis vulgaris," British Journal of Dermatology, 150:1167-1173 (2004).
Lebwohl, "The Evolution of Vitamin D Analogues for the Treatment of Psoriasis," Arch. Dermatol., 131:1323-1324 (1995).
Montalto, Jr., "A Study of the Feasibility of Polyaphrons as Transdermal Drug Delivery Systems," MS thesis; University of Rhode Island, Kingston, 1984, Print (95 pages).
Ortonne et al., "Efficacy of treatment with calcipotriol/betamethasone dipropionate followed by calcipotriol alone compared with tacalcitol for the treatment of psoriasis vulgaris: a randomized, double-blind trial," Dermatology, 2004209(4):308-313 (2004) PMID 15539894, Medline, DA 20041112, Abstract only.
International Search Report for International Application No. PCT/EP2012/054498 dated May 7, 2012.
Poyner et al., "Long Term Treatment of Chronic Plaque Psoriasis with Calcipotriol" Journal of Dermatological Treatment, 4(4):173-177 1993.
Sebba, "Preparation and Properties of Polyaphrons (Biliquid Foams)" Chemistry and Industry, Chemical Society, Letchworth, GB, No. 10, 1984, pp. 367-372.
Traulsen et al., "The Atrophogenic Potential and Dermal Tolerance of Calcipotriol/Betamethasone Dipropionate Ointment Compared with Betamethasone Dipropionate Ointment," Dermatology, 207: 166-172 (2003).
Van De Kerkhol et al., "A two-compound product containing calcipotriol and betamethasone dipropionate provides rapid, effective treatment of psoriasis vulgaris regardless of baseline disease severity", Dermatology, 210(4):294-299 (2005) (Abstract).
Van De Kerkhol et al., "Mixed treatment comparison of a two-compound formulation (TCF) product containing calcipotriol and betamethasone dipropionate with other topical treatments in psoriasis vulgaris," Current Medical Research & Opinion, 27(1):225-238 (2011).
Wheeler, "High Internal Phase Dispersions," Conference: Cosmetics and Colloids (online) Feb. 15, 2005, pp. 1-12.
JP 10-139669 A (1998) English translation of claims (2 pages).
PCT/GB2004/003329 International Search Report dated Feb. 16, 2005.
Decision of US Court of Appeals for Federal circuit, Leo Pharmaceutical Products, Ltd. Appelle, 2012-1520, Appeal from BPAI No. 95/000,153, decided Aug. 12, 2013.
Le Yan (Stability, Transport, and Applications of polyaphrons in porous media, A dissertation Submitted to the Graduate Faculty of the Louisiana State University and Agricultural and Mechanical

(56) References Cited

OTHER PUBLICATIONS

College in Partial fulfillment of the Requirements for the degree of Doctor of Philosophy, May 2005).

Lye et al.: "Immobilization of Candida cylindracea Lipase on Colloidal Liquid Aphrons (CLAs) and Development of a Continuous CLA-Membrane Reactor"; Biotechnology and Bioengineering, vol. 51, pp. 69-78 (1996).

Stuckey et al.: The Immobilisation of Enzymes on Colloidal Liquid Aphrons (CLAs) for Bi-phasic Reactions: Stability, Protein Structure, and use in Crossflow Membrane Bioreactors (2000—estimated).

\* cited by examiner

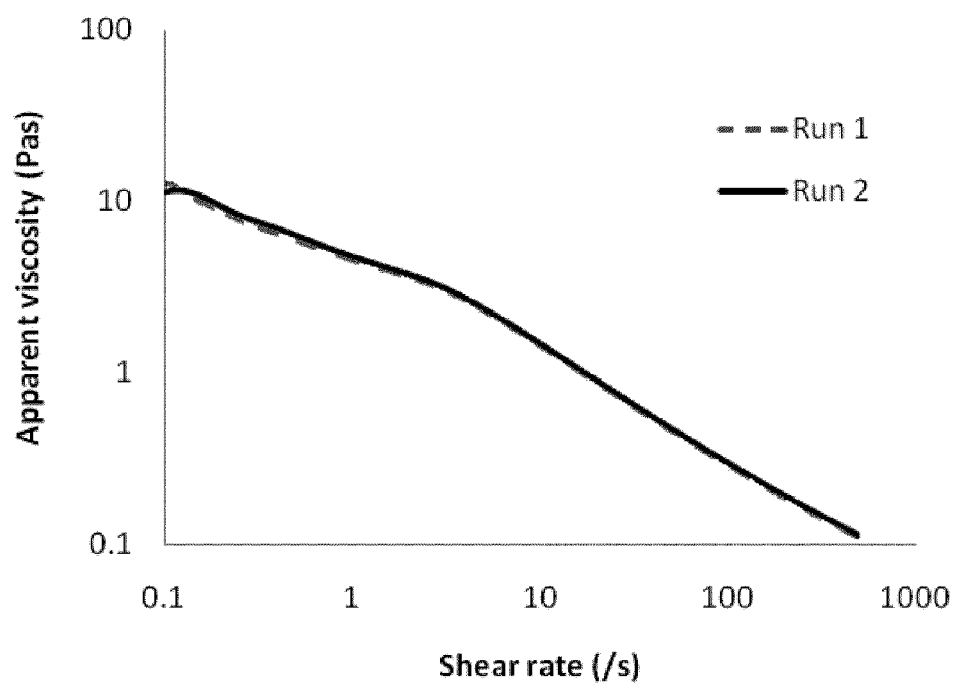

OPHTHALMIC COMPOSITION

RELATED APPLICATIONS

This application is a national phase application of, and claims priority to, PCT/EP2012/054498, filed Mar. 14, 2012, which claims priority to European Patent Application No. 11158099.9, filed Mar. 14, 2011, the disclosures of which are incorporated herein in their entirety by reference.

The present invention relates to ophthalmic compositions, and in particular to a topical ophthalmic composition comprising a polyaphron dispersion. The invention also relates to methods of making ophthalmic compositions, ophthalmic compositions for use in the treatment of the human and/or animal eye by topical application. The invention further relates to a device for dropwise dispensing the ophthalmic composition.

Ophthalmic compositions for use in the treatment of eyes are known in the art. Such compositions may, for example, contain pharmaceutically active agents and be used for the treatment of specific diseases of the eye. Alternatively, or additionally the compositions may be used as tear replacement solutions.

When the ophthalmic compositions comprise pharmaceutically active agents and/or excipients side effects are sometimes observed upon topical application of the compositions to the eye. Such side effects may be related to the dosage and/or duration of the treatment and/or the potency of the active agent. Moreover, the efficacy of the treatment may be reduced if sufficient (for example, a therapeutically active amount) of active agent cannot penetrate the eye upon treatment. For example, if the composition is not sufficiently viscous upon application to the eye, it may run off the eye before a therapeutically effective amount of active agent has penetrated the surface of the eye. Alternatively and/or additionally the effectiveness of the treatment may be reduced if the concentration of the pharmaceutically active agent is low in the composition so that in order to provide a therapeutically effective amount of the agent to the patient, repeated doses of treatment must be applied. In such cases, the efficacy of the treatment will depend on the end users compliance with a specific treatment regime. This may not be desirable as the end users compliance with such a regime may be less than adequate.

It is one object of the present invention to overcome or address the problems of prior art ophthalmic compositions or to at least provide a commercially useful alternative thereto. It is an alternative and/or additional object to provide an ophthalmic composition which is cheaper to make and/or more effective than known ophthalmic compositions.

In the first aspect of the present invention there is provided an ophthalmic composition comprising a polyaphron dispersion. Preferably the ophthalmic composition is for topical application to the human and/or animal eye. Preferably it is a topical ophthalmic composition.

The present invention will now be further described. In the following passages different aspects of the invention are defined in more detail. Each aspect so defined may be combined with any other aspect or aspects unless clearly indicated to the contrary. In particular any feature indicated as being preferred or advantageous may be combined with any other feature or features indicated as being preferred or advantageous.

In a further aspect of the present invention there is provided an ophthalmic composition according to any of the preceding claims for use in the treatment of the human and/or animal eye by topical application.

In a further aspect of the present invention there is provided a method of making the ophthalmic composition as described herein comprising the following steps:
(i) providing a hydrophilic solvent;
(ii) providing a hydrophobic solvent;
(iii) mixing the hydrophilic solvent with the hydrophobic solvent under suitable conditions to form the composition comprising a polyaphron dispersion;
wherein the hydrophilic solvent and/or the hydrophobic solvent comprises a surfactant;
and wherein the hydrophilic solvent and/or the hydrophobic solvent optionally comprises a pharmaceutically active agent.

In a further aspect of the present invention there is provided a device for dropwise dispensing of a composition, the device comprising a container holding the composition as described herein.

It is one object of the present invention to provide an ophthalmic composition which has improved patient compliance and/or reduced side effects upon application compared to known compositions. It is also desirable to provide an ophthalmic composition comprising a pharmaceutically active agent wherein upon treatment of a patient with the ophthalmic composition, the permeation of the pharmaceutically active agent from the ophthalmic composition is greater than the permeation of pharmaceutically active agents from known ophthalmic compositions.

Some of the advantages of the use of a polyaphron dispersion in ophthalmic compositions as described herein, over known ophthalmic compositions, in particular over those comprising emulsions, may be summarized below:

Lower surfactant levels
Improved safety
Higher oil levels
Easier, more controllable manufacture
More consistent form—easy to characterize to the required standard
Controllable and consistent droplet size
Wider choice of oils
Multiple pharmaceutically active agents each in its own oil
Improved stability of vulnerable pharmaceutically active agents
Controllable rheology, independent of dispersion formulation.
Lower preservative levels
Droplet size consistent upon substantial dilution The present inventors have found that one of the advantages of using polyaphron dispersions in ophthalmic compositions is that it is possible to consistently control the droplet size (and for example the size of the discontinuous phases), the rheology, the surfactant levels and the components which make up the compositions. This makes it possible to provide a composition with improved or suitable tolerability to the end user. The compositions may be tailored to exclude irritants, such as high levels of surfactants, low preservatives, and/or include beneficial components. They also provide the possibility of forming compositions having high concentrations of pharmaceutically active agents and/or additives. This is because the pharmaceutically active agents and/or additives may be present in either or both of the hydrophobic phase and/or hydrophilic phase, the discontinuous phase and/or continuous phase of the polyaphron dispersion depending for example on their solubility. This is of particular use, when the amount of pharmaceutically active agent can be increased in the composition such that with each application of the composition to the eye, an increased level of pharmaceutically active agent is administered. This means that it is possible to reduce the frequency of application of the composition, which may help with patient compliance and/or improved efficacy of the treatment of the eye condition.

The ophthalmic compositions described herein also have an advantage of potentially allowing higher levels of pharmaceutically active agent into the compositions compared to known ophthalmic compositions. This may be possible for example if the active is soluble (or at least partially soluble) in the discontinuous (preferably oil) phase of the polyaphron dispersion. Polyaphron dispersion may have higher levels of oil and still remain stable compared to other compositions, for example though comprising emulsions.

The ophthalmic compositions described herein also permit efficient and preferably improved delivery of pharmaceutically active agents and/or additives to the eye. This may be achieved by improved permeation.

Preferably the ophthalmic compositions are stable and/or have an improved stability over known products. Advantageously the compositions are stable over an extended period of time, for example over 3 months, 6 months or 9 months or 12 to 24 months. Preferably, the compositions are stable, for example, when they are stored under air-tight conditions in the final packaging for at least 3 months, more preferably at least 6 months at from 3 to 5° C., or from 20° C. to 25° C. Where a pharmaceutically active agent is present in the compositions preferably each active shall not have diminished by more than 5% by weight of the original content at the date of commencement of the storage test after 3 months of storage. Known decomposition products of the actives, if any such are present, collectively constitute no more than 5% of the original active based upon area under the curve measurements for example by HPLC analysis or other suitable analytical technique known in the art.

Preferably the ophthalmic composition as described herein has at least one or more of the following advantages over known ophthalmic compositions, which may, for example, assist in improving patient compliance:
a) convenience (e.g. reduced dosing frequency by formulating combinations of pharmaceutically active agent(s);
b) efficacy (e.g. improved penetration to increase effect at unchanged concentration or maintain effect at lower concentration); and
c) safety (better tolerability, e.g. by reducing irritating excipients and/or pharmaceutically active agent(s) in formulation).

Moreover, the ophthalmic compositions described herein achieve the described benefits whilst having low levels of surfactants. This is advantageous as surfactants may be irritants.

In the following description, the meaning of the terms used are as follows: by hydrophilic phase or solvent is meant a liquid phase comprising water, comprising water together with other water-miscible liquids, or comprising a non-aqueous liquid which is miscible with water. By hydrophobic phase or solvent is meant a phase comprising pharmaceutically acceptable liquids such as oils that are immiscible or substantially immiscible with the hydrophilic phase. By immiscible liquids is meant that when mixed together, they separate to form two distinctly separate liquid phases sharing a well-defined interface. By substantially immiscible is meant that two liquids mixed as above having a well defined interface between two phases where each phase may nevertheless contain small quantities of dissolved molecules of the other phase.

A polyaphron dispersion comprises a continuous phase, a discontinuous phase and a surfactant. It will be understood that typically a polyaphron dispersion comprises one continuous phase and a plurality of discontinuous phases. The polyaphron dispersion may comprise a hydrophobic discontinuous phase, and a hydrophilic continuous phase. Alternatively, the polyaphron dispersion may comprise a hydrophilic discontinuous phase and a hydrophobic continuous phase.

By polyaphron dispersion as used herein is meant a particular kind of hydrophilic liquid-in-hydrophobic liquid or hydrophobic liquid-in-hydrophilic liquid dispersion comprising (a) a hydrophilic liquid miscible phase, (b) a second hydrophobic phase being immiscible or substantially immiscible with the first phase and (c) one or more surfactants, wherein the dispersed or discontinuous phase is in the form of small (e.g. micron to sub-micron diameter, but more usually at least 1 micron diameter) droplets, and the whole having the following characteristics, which distinguish polyaphron dispersions from conventional or common emulsions and other dispersion types:

1. They are capable of existing in a stable form wherein the volume fraction of the dispersed phase ($\phi_{ip}$) is greater than 0.7 and can be as high as 0.97 ($\phi_{ip}$ is the volume ratio of discontinuous to continuous phase expressed as a fraction).
2. The microscopic appearance of polyaphron dispersions where $\phi_{ip}$ is greater than 0.7 is that of an aggregate of individual droplets, pushed closely together into polyhedral shapes, resembling the appearance of a gas foam. In this form, the dispersion has gel-like properties and is referred to as a Gel Polyaphron Dispersion (GPD).
3. Stable polyaphron dispersions can be formed with a surfactant concentration less than 3% and more typically less than 2% by weight of the total composition.
4. Gel Polyaphron Dispersions (as described in 2 above) can be diluted to any extent by the addition of more continuous phase without the addition of more surfactant, when the gel-like properties disappear. Once $\phi_{ip}$ has been reduced to below 0.7, the individual droplets of internal phase become separated to take the form of spherical droplets, which remain stable and intact but which may nevertheless join together in loose associations and float to the top or sink to the bottom of the diluted dispersion (depending on the relative densities of the two phases). In this diluted form each droplet is referred to as a Colloidal Liquid Aphron (CLA). Simple shaking of the diluted dispersion instantly causes a homogeneous, stable dispersion of Colloidal Liquid Aphrons to re-form.

Each of the above characteristics and a combination of them clearly differentiate the polyaphron dispersions of the present invention from conventional emulsions and other dispersion types which do not have all of those characteristics. Polyaphron dispersions are disclosed in the following literature references by Sebba: "Biliquid Foams", J. Colloid and Interface Science, 40 (1972) 468-474 and "The Behaviour of Minute Oil Droplets Encapsulated in a Water Film", Colloid Polymer Sciences, 257 (1979) 392-396, Hicks "Investigating the Generation, Characterisation, and Structure of Biliquid Foams", PhD Thesis, University of Bristol, 2005, Crutchley "The Encapsulation of Oils and Oil Soluble Substances Within Polymer Films", PhD Thesis, The University of Leeds, 2006 and Lye and Stuckey, Colloid and Surfaces, 131 (1998) 119-136. Aphrons are also disclosed in U.S. Pat. No. 4,486,333 and WO 97/32559.

Polyaphron dispersions are sometimes referred to as 'Biliquid Foams', 'High Internal Phase Emulsions (HIPEs)', 'High Internal Phase Ratio Emulsions (HIPREs)' and 'Gel Emulsions'. In U.S. Pat. No. 5,573,757 a composition comprising a polyaphron dispersion is described as "a viscoelastic gel". All descriptions that refer to dispersions having the characteristics described above are polyaphron dispersions as used in the present invention.

The term "topical composition" and "topical formulation" are used herein interchangeably. When the topical composition comprises an active ingredient(s), it refers to a composition formulated such that the active ingredient(s) of the composition may be applied by direct administration to the surface of the eye and from which an amount of the active ingredient(s) is released. Examples of topical formulations include, but are not limited to, lotions, sprays, hydrogels, aerosols, foams, ointments, creams, gels, pastes, and the like. The term "topical", when used herein to characterize the delivery, administration or application of a composition of the present invention, is meant to specify that the composition is delivered, administered or applied directly to the site of interest (i.e., to the eye) for a localized effect. Preferably, topical administration is effected without any significant absorption of components of the composition into the subject's blood stream (to avoid a systemic effect). In certain preferred embodiments of the present invention, topical administration of a composition is effected without any significant absorption of components of the composition into the subject's eye tissues, such as the aqueous humor, and corneal and conjunctival tissues.

Preferably the composition is administered directly to the cornea and/or instilled into the anterior portion of the eye. The composition may be administered to effect therapeutic benefit to other parts of the eye, for example to goblet cells, lacrimal glands, oil secreting glands and/or nasolacrimal ducts.

The term "non-invasive", when used herein refers to a method or mode of administration that does not rupture or puncture (e.g., by a mechanical means) of a biological membrane to which a composition, optionally comprising a pharmaceutically active agent, is being delivered. Preferably, the ophthalmic composition as described herein is administered by non-invasive routes or procedures.

The term "ophthalmic", as used herein in connection with a composition, refers to a composition intended to be administered to the eye and which preferably provides a pharmaceutical effect, preferably to the eye.

The terms "therapeutic agent", "drug", and "pharmaceutically active agent" are used herein interchangeably. They refer to a substance, molecule, compound, agent, factor or composition effective in the treatment of a disease or condition.

The ophthalmic compositions as described herein may be formulated using any pharmaceutically acceptable carriers and/or excipients suitable for topical administration to the eye surface.

In one embodiment the ophthalmic composition as described herein is not for use in tear replacement therapy, nor for use as a tear substitute, nor is it for use in a tear replacement solution. In one embodiment, the ophthalmic composition as described herein is for use in treating diseases of the eye with the proviso that it is not for use in treating "dry-eye". Preferably the ophthalmic composition as described herein comprises a pharmaceutically active agent and is for use in the treatment of diseases of the human and/or animal eye, which are treatable by topical application of said pharmaceutically active agent.

As described above, a polyaphron dispersion comprises a continuous phase, at least one discontinuous phase and a surfactant. The polyaphron dispersion may comprise a hydrophobic discontinuous phase (typically a plurality of hydrophobic discontinuous phases), and a hydrophilic continuous phase. Alternatively, the polyaphron dispersion may comprise a hydrophilic discontinuous phase (typically a plurality of hydrophilic discontinuous phases), and a hydrophobic continuous phase.

Preferably, the discontinuous phase comprises a hydrophobic solvent and the continuous phase comprises a hydrophilic solvent. Preferably the discontinuous phase is a hydrophobic discontinuous phase comprising one or more hydrophobic solvents and substantially no hydrophilic solvents. Preferably the continuous phase is a hydrophilic continuous phase comprising one or more hydrophilic solvents and substantially no hydrophobic solvents. Typically a plurality of discontinuous phases are present in the composition.

In another embodiment of the present invention the continuous phase comprises a hydrophobic solvent and the discontinuous phase comprises a hydrophilic solvent.

Preferably the continuous phase is a hydrophobic continuous phase comprising one or more hydrophobic solvents and substantially no hydrophilic solvents. Preferably the discontinuous phase is a hydrophilic discontinuous phase comprising one or more hydrophilic solvents and substantially no hydrophobic solvents. Typically a plurality of discontinuous phases are present in the composition.

The discontinuous phase is preferably a substantially hydrophobic internal phase, commonly known as an oil internal phase. Preferably, the hydrophobic phase, which is preferably the discontinuous phase, comprises a pharmaceutically acceptable oil phase.

Examples of oils which may be used in the present invention include almond oil, babassu oil, blackcurrant seed oil, borage oil, canola oil, castor oil, coconut oil, cod liver oil, corn oil, cottonseed oil, evening primrose oil, fish oil, grapeseed oil, mustard seed oil, oat oil, olive oil, palm kernel oil, palm oil, peanut oil, rapeseed oil, safflower oil, sesame oil, shark liver oil, squalane, soybean oil, sunflower oil, walnut oil, wheat germ oil, hydrogenated castor oil, hydrogenated coconut oil, hydrogenated cottonseed oil, hydrogenated palm oil, hydrogenated soybean oil, partially hydrogenated soybean oil, hydrogenated vegetable oil, isopropyl myristate, isopropyl isostearate, isopropyl palmitate, modified triglycerides, caprylic/capric glycerides, caprylic/capric triglyceride, fractionated triglycerides, glyceryl tricaprate, glyceryl tricaproate, glyceryl tricaprylate, glyceryl tricaprylate/caprate, glyceryl tricaprylate/caprate, glyceryl tricaprylate/caprate/laurate, glyceryl tricaprylate/caprate/linoleate, glyceryl tricaprylate/caprate/stearate, glyceryl trilaurate, glyceryl trilinoleate, glyceryl trilinolenate, glyceryl trioleate, glyceryl triundecanoate, linoleic glycerides, saturated polyglycolized glycerides, synthetic medium chain triglyceride containing primarily $C_8$-$C_{12}$ fatty acid chains, medium chain triglycerides, long chain triglycerides, modified triglycerides, fractionated triglycerides, silicones, phospholipids and mixtures thereof.

Long chain triglycerides as used herein includes a glycol triester where the acid moieties are saturated, monounsaturated or polyunsaturated fatty acids with a chain of 14 to 20 carbon atoms. Typical fatty acid moieties are oleic acid, stearic acid and linoleic acid.

Suitably the hydrophobic phase comprises one or more monoglycerides, diglycerides, triglycerides or mixtures thereof. Preferably the one or more monoglycerides, diglycerides, triglycerides are glycol esters of fatty acids containing from 6 to 22 carbon atoms.

In a preferred embodiment the hydrophobic phase is selected from the group consisting of castor oil, long chain triglycerides, medium chain triglycerides, mineral oil, silicones, phospholipids, mono- and diglycerides and mixtures of two or more thereof.

Preferably the composition comprises one or more fatty acids containing from 6 to 22 carbon atoms. More preferably, the composition comprises omega-3 fatty acids. Omega-3 fatty acids are long-chain polyunsaturated fatty acids (18-22 carbon atoms in chain length) with the first of the double bonds ("unsaturations") beginning with the third carbon atom from the methyl end of the molecule. They are called "polyunsaturated" because their molecules have two or more double bonds "unsaturations" in their carbohydrate chain. They are termed "long-chain" fatty acids since their carbon backbone has at least 18 carbon atoms. In addition to stearidonic acid "SDA" the omega-3 family of fatty acids includes alpha-linolenic acid ("ALA"), eicosatetraenoic acid (ETA), eicosapentaenoic acid ("EPA"), docosapentaenoic acid (DPA), and docosahexaenoic acid ("DHA").

Preferably the ophthalmic composition does not comprise a fluorocarbon and/or silicone oil.

The discontinuous phase may, for example, confer an emollient, occlusive, moisturising, conditioning or other cosmetic or pharmaceutical benefit to the eye. It may also increase the viscosity of the composition and may confer solvency to the active or actives. It may contain materials providing a heating or cooling effect when applied to the eye (for example capsaicin or menthol).

The composition may comprise at least 5% by weight of the discontinuous phase, more preferably at least 2% by weight, the discontinuous phase based on the weight of the total composition.

The composition may comprise less then 15% by weight of the discontinuous phase, more preferably less than 5%, less than 4%, less than 2%, less than 1%, less than 0.5% by weight of discontinuous phase based on the weight of the total composition. Unlike topical compositions for use of the skin where it is advantageous to have high levels of discontinuous phase, (preferably oil phases), in the described ophthalmic compositions, in some embodiments it is advantageous to comprise much lower levels. As the eye is very sensitive, when an active agent is present in the composition, low levels of active agents are typically sufficient to treat the eye condition. One advantage of using polyaphron dispersions is that unlike emulsions a low percentage (such as those outlined above) of discontinuous phases may be present in the composition and it can still be stable. Polyaphron dispersions tolerant high levels of dilution. Preferably the discontinuous phase comprises a pharmaceutically acceptable oil.

The hydrophilic phase (which may be the continuous phase) may comprise or consist essentially of a pharmaceutically acceptable liquid that is miscible or substantially miscible with water, preferably a compound of formula $R_1$—OH where $R_1$ is $C_1$-$C_{10}$ alkyl and/or a compound of formula HO—$R_2$—H where $R_2$ is —$(C_2H_4)_n$— or —$(C_3H_6)_n$— where n is 1 to 100, preferably 1 to 25. $R_1$ and $R_2$ may be linear or branched. Preferably $R_1$ is $C_1$-$C_4$ alkyl. n is preferably 1 to 25. Preferably the hydrophilic phase comprises propylene glycol, polyethylene glycol, glycerol, ethanol, isopropyl alcohol, or a mixture thereof. Where the hydrophilic phase comprises polyethylene glycol or polypropylene glycol, the polyethylene or polypropylene glycol is preferably a polyethylene glycol which is liquid at room temperature (20° C.). The polyethylene glycol may, for example, contain from 1 to 12 ethylene or propylene oxide units and/or have a molecular weight of up to 600.

It will be understood that other suitable hydrophilic solvents may be used.

The composition may comprise at least 95% by weight of the continuous phase, more preferably at least 98% by weight, the continuous phase based on the weight of the total composition.

Preferably the ophthalmic composition comprises water. Preferably, the hydrophilic phase is or comprises water. The compositions of the present invention may be non-aqueous, substantially non-aqueous or aqueous.

By the term "non-aqueous" as used herein is meant a composition which is effectively free of water and does not contain water that has been deliberately added. Preferably, a "non-aqueous" composition as used herein has less than 0.5% by weight of water based on the total weight of the composition, more preferably less than 0.2% by weight of water, most preferably less than 0.1% by weight of water based on the total weight of the composition.

By the term "substantially non-aqueous" as used herein is meant a composition comprising less than 5% by weight, more preferably less than 4.5% by weight, of water based on the total weight of the composition.

By the term "aqueous" is meant a composition comprising at least 5%, at least 10%, or at least 15% by weight of water based on the total weight of the composition.

In one embodiment the composition comprises at least 85% by weight of water, at least 90% by weight of water, at least 95% by weight of water or at least 98% by weight of water based on the total weight of the composition. It may be advantageous for the composition to comprise high levels of water if the composition is to be administered to the eye without further dilution. Additionally, having high levels of water decreases the potential risk of irritation to the eye caused by other components present in the composition.

Suitable pharmaceutically acceptable excipients may be present in the composition.

The pH of the composition and preferably the pH of the hydrophilic phase (which is preferably the continuous phase) is preferably from 3.5 to 9, or from 5 to 8, more preferably still to a pH of from 6 to 7.5. It will be understood that any suitable acid or base may be used to adjust the pH to the appropriate value or pH range. Preferably, the pH of the hydrophilic phase is adjusted as required after addition of the hydrophobic phase(s). The pH of the composition may be adjusted after addition of the polyaphron dispersion. Typically the pH of the composition will need to be raised by the addition of a base, which suitably may sodium hydroxide. Advantageously and preferably, the pH of the composition may be stabilized by the incorporation of a suitable buffer into the aqueous phase. Suitable buffer systems having a pH within the specified range will be familiar to those skilled in the art, and include for example sodium citrate buffer.

The surfactant(s) used in the present invention may be incorporated into either or both phases of the polyaphron dispersion. The surfactant may be selected from the group consisting of non-ionic surfactants, cationic surfactants, anionic surfactants, zwitterionic surfactants and mixtures of two or more thereof.

In one embodiment, preferably, the polyaphron dispersion comprises at least one non-ionic surfactant. Preferably at least one non-ionic surfactant is present in the hydrophilic and/or hydrophobic phase of the present invention. The polyaphron dispersion may comprise further non-ionic and or ionic surfactants.

Suitable surfactants include an alkyl polyglycol ether, an alkyl polyglycol ester, an ethoxylated alcohol, a polyoxyethylene sorbitan fatty acid ester, a polyoxyethylene fatty acid ester, an ionic or non-ionic surfactant, a hydrogenated castor oil/polyoxyethylene glycol adduct containing from 25 to 60 ethoxy groups a castor oil/polyoxyethylene glycol adduct containing from 25 to 45 ethoxy groups, a sorbitan fatty acid ester (for example Span 20 or Span 80), a block copolymer of ethylene oxide and propylene oxide (for example Pluronic L121 or Pluronic F68), or a mixture thereof.

Suitable non-ionic surfactants include poloxamers, tyloxapol, polysorbates polyoxyethylene castor oil derivatives, sorbitan esters, and mixtures of two or more thereof.

Suitable cationic surfactants include hexadecyl trimethyl ammonium bromide, CTAB and mixtures of two or more thereof.

Suitable anionic surfactants include sodium lauryl ether sulphate (SLES), sodium lauryl sulphate and mixtures of two or more thereof.

Suitable zwitterionic surfactants include such as phospholipids, for example lecithin, dipalmitoylphosphatidylcholine (DpPC) and mixtures of two or more thereof.

Preferably, the composition of the present invention does not comprise a fluorinated surfactant. Preferably the composition does not comprise a surfactant which comprises a fluorine atom. More preferably still, the composition as described herein does not comprise a fluorinated surfactant prepared according to the general formula: $R_F$—$R_{pol}$ where $R_F$ represents a linear or branched perfluoroalkyl group having more than 5 carbon atoms and $R_{pol}$ represents a polar hydrocarbond residue which comprises at least one functional group chosen from the series: CO—NH(R), CO—NH(R)$_2$, COO—, COOR, SO$_3$—, SO$_2$—N(R)$_2$, CH$_2$—O—, R, PO$_2$H, PO$_3$H$_2$, where R represents an alkyl.

Preferred surfactants are non-ionic, non-halogenated surfactants. It is has been found that polyaphron dispersions comprising non-ionic halogenated surfactants (and in particular those mentioned above) may break down under the shear stress (leading to irreversible decomposition of the polyaphron) caused by blinking of the eyelid when the composition is in place in the eye. This may particularly be the case when the polyaphron dispersions have been formed via a gas-foam intermediate. In contrast to this the present inventors have surprisingly found that non-ionic, non-halogenated surfactants and/or polyaphrons made using methods described below which do not require the formation of a gas-foam intermediate, typically do not break down under the shear stress caused by blinking of the eyelid when the composition is in place in the eye. This is shown in FIG. 1. In some cases it is advantageous for the composition and the surfactant to remain intact under the shear stress conditions experienced in the eye. This is particularly so when the composition comprises a pharmaceutically active agent. When the composition comprises a pharmaceutically active agent, one advantage of the present invention is that the active agent may be released from the ophthalmic composition in a controlled manner, for example by diffusion from the polyaphron dispersion (and typically by diffusion from the hydrophobic, preferably the oil phase). If the polyaphron dispersion breaks down under the shear conditions experienced in the eye the pharmaceutically active agent is not delivered in a controlled manner over time. Instead, the active is suddenly released into the eye as the polyaphron dispersion irreversibly breaks down. In contrast to this, it is preferable if the active is released in a controlled manner over time. Another advantage of the polyaphron not breaking down under shear is that the risk of damage to the composition during transport and storage is reduced.

A further advantage of the polyaphron dispersion not breaking down (or substantially not breaking down) under the conditions experienced in the eye is that the risk of any pharmaceutically active agent dissolved and/or dispersed therein precipitating is reduced. If, for example, a pharmaceutically active agent is dissolved and/or dispersed in the discontinuous phase (preferably the hydrophobic (preferably the oil)) phase of the composition and the polyaphron breaks down under the shear conditions experienced in the eye, the pharmaceutically active agent may precipitate as it is expelled rapidly from the polyaphron dispersion into the eye. The risk of precipitation is reduced by the controlled release of the pharmaceutically active agent from the polyaphron dispersion where it remains in tact in the eye.

Examples of classes of surfactants which are particularly useful in this invention include: polyethylene glycol sorbitan fatty acid esters (TWEENs, (polyoxyethylene (20) monolaurate), for example TWEEN 20 TWEEN 60 (polyoxyethylene (20) monostearate), TWEEN 80 (polyoxyethylene (20) monooleate)); sorbitan fatty acid esters (SPANs, for example SPAN 20 (sorbitan monolaurate), SPAN 40 (sorbitan monopalmitate), SPAN 80 (sorbitan monooleate)); polyethylene glycol fatty acid ethers (BRIJs, for example BRIJ 35 (polyoxyethylene (20) lauryl ether), BRIJ 58(polyoxyethylene (20) cetyl ether)); polyethylene glycol stearate esters (MRYJs, for example MYRJ S40 polyoxyethylene (40) stearate, MYRJ S50 polyoxyethylene (50) stearate,); polyoxyethylene glycol-block-polypropylene glycol-block-polyoxyethylene glycol-block (Poloxamers, such as polyoxyethylene glycol (80)-polypropylene glycol (27)-polyoxyethylene glycol (80) (Poloxamer 188) and polyoxyethylene glycol (101)-polypropylene glycol (56)-polyoxyethylene glycol (101) (poloxamer 407)) polyethylene glycol lauryl esters (Laureths, for example polyethylene glycol (4) lauryl ester (Laureth 4) and polyethylene glycol (23) lauryl ester (Laureth 23)) and mixtures of two or more thereof. One or more of each type of surfactant may be present in the composition. Additionally or alternatively mixtures of different types of surfactant may be present in the composition. One of the reasons these surfactants are particularly preferred is because of their low irritation potential. The present inventors have also surprisingly found that the above surfactants provide good shear stability over other known surfactants.

It will be understood that other suitable surfactants may be used.

Preferably the compositions of the present invention comprise less than 0.5% by weight of surfactant, more preferably less than 0.25%, more preferably still less than 0.1% by weight of the total composition. The compositions described herein may comprise less than 0.075% by weight or less than 0.05% by weight or 0.01% by weight of surfactant based on the weight of the total composition.

Preferably, the polyaphron dispersion used in the described composition comprises less than 5% by weight of surfactant based on the total weight of the polyaphron dispersion. More preferably, the polyaphron dispersion comprises less than 3%, less than 2%, or less than 1% by weight of surfactant based on the total weight of the polyaphron disperion.

Typically in order to form the described composition the polyaphron dispersion is diluted by for example from approximately 80%, 90% or 95% by weight discontinuous phase (preferably oil phase) based on the total composition (which is then the polyaphron dispersion) to approximately 1%, 2% or 5% by weight discontinuous phase (preferably oil phase) based on the total composition. Thus, the surfactant level in the final composition is typically low.

As outlined above, it is desirable for low levels of surfactant to be present in the composition as surfactants may act as irritants to the end user upon application to the eye.

Preferably, the weight ratio of discontinuous phases (which preferably are the hydrophobic phases) in the composition to total surfactant in the composition is 40 to 180. More preferably, the weight ratio of discontinuous phases (which preferably are the hydrophobic phases) in the composition to total surfactant in the composition is 50 to 120. More preferably still, the weight ratio of discontinuous phases (which preferably are the hydrophobic phases) in the composition to total surfactant in the composition is 60 to 90.

Using low levels of surfactant is advantageous for at least the following reasons:
1. Less potential to cause eye irritation to the eye itself as well as to the surrounding areas of the eye that contact the formulation in the course of application;

2. More efficient use of any preservative present in the composition as it is not locked away in micelles formed from excess surfactant. This in turn leads to less eye irritation (preservatives have significant potential irritants); and/or
3. Less potential to cause partitioning and transport of oil soluble pharmaceutically active agents into surfactant micelles, avoiding issues with solubility and also stability with vulnerable pharmaceutically active agents.

Preferably the ophthalmic composition comprises a pharmaceutically active agent. Preferably, the pharmaceutically active agent is selected from antihistamines, betablockers, corticosteroids, prostaglandins, non-steroidal anti-inflammatory drugs (NSAIDs), immune modulators, anaesthetics, antibiotics, carbonic anhydrase inhibitors, vasoconstrictors and mixtures of two or more thereof. One or more of each type of pharmaceutically active agent may be present in the composition. Additionally or alternatively mixtures of different types of pharmaceutically active agents may be present in the composition.

As well as the pharmaceutically active agents listed above, the pharmaceutically active agent may additionally and/or alternatively be selected from the group consisting of an antifungal, an opthalmological, an anti-infective, an anti-inflammatory agent, an antiglaucoma agent, an antiglaucoma miotic, a mydriatic, a cycloplegic, a decongestant, an anti-allergic, a local anesthetic, a diagnostic agent, a surgical aid, an ocular vascular disorder agent and mixtures of two or more thereof. One or more of each type of pharmaceutically active agent may be present in the composition. Additionally or alternatively mixtures of different types of pharmaceutically active agents may be present in the composition.

Compositions of the present invention may optionally further comprise at least one additional pharmaceutically active substance or agent.

The composition may comprise two or more distinct discontinuous phases made up from different components, for example from different oils. The composition may comprise one or more pharmaceutically active substances or agents in distinct discontinuous phases.

The pharmaceutically active agent may be present in the hydrophilic and/or hydrophobic phase of the polyaphron dispersion. In one embodiment at least 50%, at least 80% or at least 90% by weight of the pharmaceutically active agent present in the composition is in the hydrophilic phase. In another embodiment at least 50%, at least 80% or at least 90% by weight of the pharmaceutically active agent present in the composition is in the hydrophobic phase.

Preferably the ophthalmic composition comprises cyclosporine. Such a composition may be advantageous because it may be formulated to be non-irritating. Such a composition is suitable for use in the treatment of conditions associated with keratoconjuctivitis sicca (severe dry eye).

Cyclosporins are a group of nonpolar cyclic oligopeptides with known immunosuppressant activity. Cyclosporin A, along with several other minor metabolites, as well as cyclosporin B, C, D, E, F, G, H, I, J, K, L, M, N, O, P, Q, R, S, T, U, V, W, X, Y and Z, have been identified. In addition, derivatives, salts and the like of such cyclosporins and a number of synthetic analogs have been prepared and may be useful in the present invention.

In general, commercially available cyclosporins may contain a mixture of several individual cyclosporins which all share a cyclic peptide structure consisting of eleven amino acid residues with a total molecular weight of about 1,200, but with different substituents or configurations of some of the amino acids.

As used here, a "cyclosporin" includes any individual member of the cyclosporin group, salts thereof, derivatives thereof, analogs thereof and mixtures thereof, as well as mixtures of two or more individual cyclosporins salts thereof, derivatives thereof, analogs thereof and mixtures thereof.

In one embodiment, the cyclosporin comprises cyclosporin A, a derivative of cyclosporin A, a salt of cyclosporin A, and/or mixtures thereof.

Cyclosporin A has the chemical name cyclo[[(E)-(2S,3R,4R)-3-hydroxy-4-methyl-2-(methylamino)-6-octenoyl]-L-2-aminobutyryl-N-methylglycyl-N-methyl-L-leucyl-L-valyl-N-methyl-L-leucyl-L-alanyl-D-alanyl-N-methyl-L-leucyl-N-methyl-L-leucyl-N-methyl-L-valyl]. The chemical structure for cyclosporin A is represented by Formula 1.

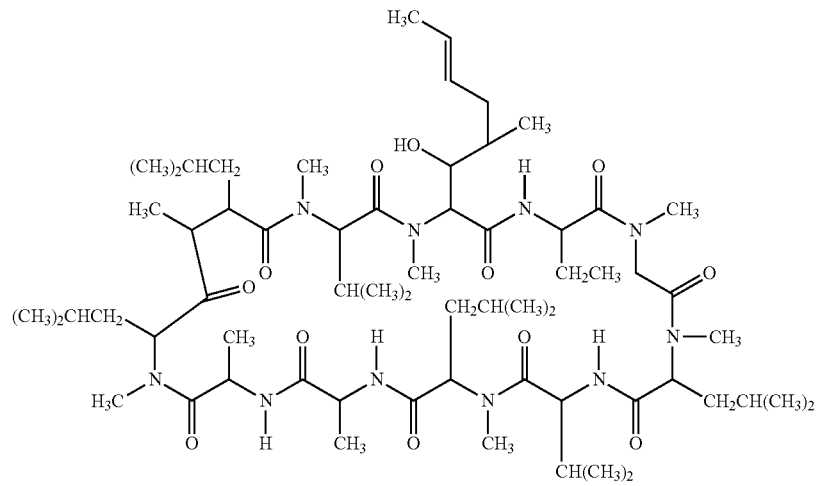

Formula I

As used here, the term "derivatives" of a cyclosporin refer to compounds having structures sufficiently similar to the cyclosporin so as to function in a manner substantially similar to or substantially identical to cyclosporin A.

Included, without limitation, within the useful cyclosporin A derivatives are those selected from ((R)-methylthio-Sar)³-(4'-hydroxy-MeLeu) cyclosporin A, ((R)-(Cyclo)alkylthio-Sar)³-(4'-hydroxy-MeLeu)⁴-cyclosporin A, and ((R)-(Cyclo)alkylthio-Sar)³-cyclosporin A derivatives described below.

These cyclosporin derivatives are represented by the following general formulas (II), (III), and (IV) respectively:

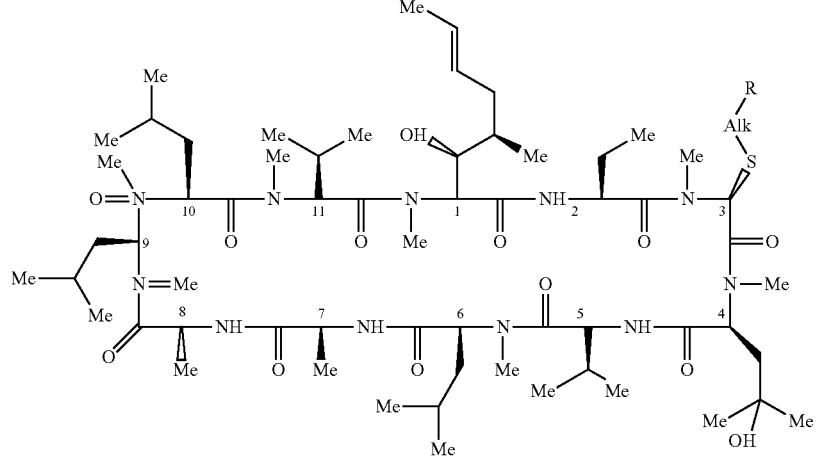

Formula II

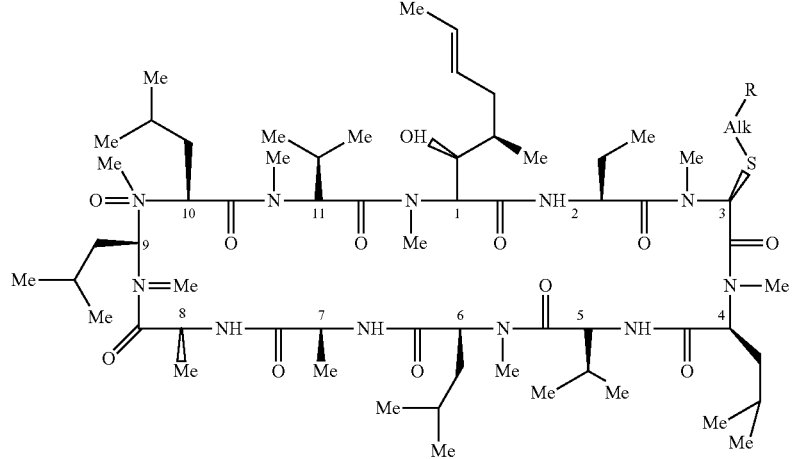

Formula III

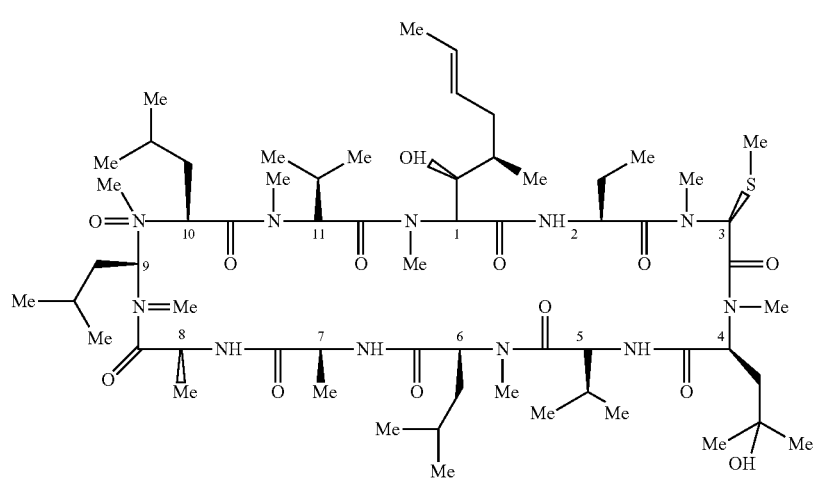

Formula IV wherein Me is methyl; Alk is 2-6C alkylene or 3-6C cycloalkylene; R is OH, COOH, alkoxycarbonyl, —NR$_1$R$_2$ or N(R$_3$)—(CH$_2$)—NR$_1$R$_2$; wherein R$_1$, R$_2$ is H, alkyl, 3-6C cycloalkyl, phenyl (optionally substituted by halo, alkoxy, alkoxycarbonyl, amino, alkylamino or dialkylamino), benzyl or saturated or unsaturated heterocyclyl having 5 or 6 members and 1-3 heteroatoms; or NR$_1$R$_2$ is a 5 or 6 membered heterocycle which may contain a further N, O or S heteroatom and may be alkylated; R$_3$ is H or alkyl and n is 2-4; and the alkyl moieties contain 1-4C.

In one embodiment of the present invention the composition does not comprise cyclosporine (for example, cyclosporine A or a cyclosporine derivative or a cyclosporine salt).

In one embodiment of the present invention the composition does not comprise a vitamin D and/or a vitamin D analogue and/or a corticosteroid.

Preferably the ophthalmic composition comprises hyaluronic acid and/or pharmaceutically acceptable salts and/or derivatives thereof.

In one embodiment the ophthalmic composition comprises cyclosporine and hyaluronic acid and/or pharmaceutically acceptable salts and/or derivatives thereof.

Preferably the ophthalmic composition comprises Flurbiprofen and/or pharmaceutically acceptable salts and/or derivatives thereof.

The ophthalmic composition may comprise Vancomycin, Fluticasone, Latanoprost, Cyclosporin, Ketotifen, propanolol, flurbiprofen, Clotrimazole, pharmaceutically acceptable salts of any of the above, derivatives of any of the above and mixtures of two or more thereof.

Examples of suitable actives for use in the compositions described herein for treating specific conditions are given below.

| Class of active | Example active | condition |
|---|---|---|
| Beta-adrenergic receptor blocker | ketotifen | glaucoma |
| Immune suppressant | cyclosporine | dry eye |
| Prostaglandin | latanoprost | glaucoma |
| Antihistamine | propranolol | allergic conjunctivitis |
| Antibiotic | vancomycin | bacterial infections, chalazion, stye |
| Corticosteroid | fluticasone | ocular inflammation, blepharitis, Behçet's disease, uveitis |

Pharmaceutically acceptable salts, isomers, esters and derivatives thereof and bases may be substituted for any of the pharmaceutically active agents or drugs described herein. Mixtures of pharmaceutically active agents may be used where therapeutically effective.

The ophthalmic composition of the present invention is preferably presented in a unit dosage form. Each unit dosage may comprise from 0.0025 mg to 500 mg, and in particular from 1 mg to 100 mg, of the pharmaceutically active agent. It will be understood that the preferred unit dosage will depend on the particular pharmaceutically active agent used, or the particular combination of pharmaceutically active agents used, and the method of application of the dosage.

When the composition as described herein comprises a pharmaceutically active agent, the pharmaceutically active agent is preferably present in an effective amount. As used herein, the term "effective amount", refers to any amount of a compound, agent or composition that is sufficient to fulfill its intended purpose (s), e.g., a desired biological or medicinal response in a tissue, system or subject. For example, in certain embodiments of the present invention, the purpose (s) may be: to slow down or stop the progression, aggravation, or deterioration of the symptoms of an eye disease or condition, to bring about amelioration of the symptoms of the disease or condition, and/or to cure the disease or condition. Determination of an effective amount is well within the ordinary skill in the art of pharmaceutical sciences and medicine, in that it may depend on various biological factors or individual variations and response to treatments.

The term "pharmaceutically acceptable carrier or excipient" refers to a carrier medium which does not interfere with the effectiveness of the biological (or pharmaceutical) activity of the active ingredient (s) and which is preferably not excessively toxic to the host at a concentration at which it is administered.

The composition may comprise additives such as inert diluents, buffering agents, dispersing or wetting agents, preservatives, chelating agents, anti-foaming agents, antioxidants, permeation enhancers, gelling agents, rheology modifying agent, such as viscosity modifier(s), tonicity agents and combinations of one or more thereof. These additives may be included in the continuous and/or the discontinuous phase of the polyaphron dispersion and/or they may be added to the composition after polyaphron formation.

Inert diluents may be sucrose, sorbitol, sugar, mannitol, microcrystalline cellulose, starches, calcium carbonate, sodium chloride, lactose, calcium phosphate, calcium sulfate, or sodium phosphate.

Examples of buffering agents include citric acid, acetic acid, lactic acid, hydrogenophosphoric acid, diethylamine, sodium hydroxide and tromethane (i.e., tris-(hydroxymethyl)aminomethane hydrochloride).

Examples of dispersing or wetting agents are naturally occurring phosphatides (e.g., lecithin or soybean lecithin), condensation products of ethylene oxide with fatty acids or with long chain aliphatic alcohols (e.g., polyoxyethylene stearate, polyoxyethylene sorbitol monooleate, and polyoxyethylene sorbitan monooleate).

Preservatives may be added to a composition of the invention to prevent microbial contamination that can affect the stability of the formulation and/or cause infection in the patient. Suitable examples of preservatives include parabens (such as methyl, ethyl, propyl, p-hydroxybenzoate, butyl, isobutyl, and isopropylparaben), potassium sorbate, sorbic acid, benzoic acid, methyl benzoate, phenoxyethanol, bronopol, bronidox, MDM hydantoin, iodopropynyl butylcarbamate, benzalconium chloride, cetrimide, and benzylalcohol. Preferred preservatives include benzalkonium chloride, benzododecinium bromide, PURITE (stabilized oxychloro complex), methyl-, butyl-, propyl-parabens and mixtures of two or more thereof.

Preferably the composition comprises less than 0.05% by weight of preservative based on the total weight the composition. More preferably the composition comprises less than 0.02%, less than 0.01% or less than 0.005% by weight of preservative based on the total weight the composition.

Examples of chelating agents include sodium EDTA and citric acid.

Anti-foaming agents usually facilitate manufacture of pharmaceutical compositions, they dissipate foam by destabilizing the air-liquid interface and allow liquid to drain away from air pockets. Examples of anti-foaming agents include simethicone, dimethicone, ethanol, and ether.

Suitable antioxidants include, but are not limited to butylated hydroxyanisole (BHA), butylated hydroxytoluene, ascorbic acid, sodium metabisulphite, propyl gallate, sodium thiosulphate, alpha-tocopherol, ascorbic acid, retinoic acid, lutein, derivatives, precursors or prodrugs thereof, and mixtures of two or more thereof. Preferred antioxidants are butylated hydroxyanisole (BHA) and butylated hydroxytoluene. Addition of antioxidants may be advantageous in extending the shelf-life of the compositions.

One or more permeation enhancers may be added to the composition to improve delivery, for example to the posterior section, of the eye.

Suitable permeation enhancers include propylene glycol. Other suitable ocular permeation enhancers may be selected from one or more and mixtures of the following non-exhaustive list:

Surfactants: Sorbitan glycerides (SPAN 20, polyoxyethylene sorbitan glycerides 40, 85); (TWEEN 20, 40, 81); polyethylene glycol 1000 stearate (Aptet 100); G 1045; polyoxyethylene stearyl ethers (BRIJ 23, 35, 48, 58, 78, 98); polyoxyethylene stearate (MYRJ S40, S50); polyoxyethylene castor oil (CREMOPHOR EL); BL-9; polyoxyethylene p-(tetramethylbutyl)phenyl ether (TRITON X-100); saponin Bile acids and bile salts: Deoxycholic acid; taurocholic acid; taurodeoxycholic acid; urodeoxycholic acid; tauroursodeoxycholic acid; sodium cholate; sodium glycocholate Fatty acids: capric acid Preservatives: benzalkonium chloride; benzododecinium bromide; chlorhexidine digluconate; benzyl alcohol; chlorbutanol; 2-phenylethanol; paraben; propyl paraben Chelating agents: EDTA Others: 1-dodecylazacycloheptan-2-one (Azone); hexamethylene lauramide; hexamethylene octanamide; decylmethylsulfoxide; PHARMASOLVE (N-methyl pyrolidone); GELUCIRE 44/14 (Lauroyl macrogol-32 glycerides); borneol; dimethyl sulphoxide; sodium fusidate; decamethonium bromate; cetyl pyridinium chloride; a-amino acids; cyclodextrins; medium chain monoglycerides; cetrimide; cytochalasins Particularly preferred permeation enhancers are BRIJ 58, Azone, β-cyclodextrin, cetrimide and mixtures of two or more thereof.

The ophthalmic composition may comprise one or more tonicity agents. Suitable tonicity agents include one or more of sorbitol, glycerine, sodium chloride and dextrose.

The tonicity agent may be selected from the group consisting of a salt, a sugar, a sugar alcohol, a glycol, a carbamide and mixtures of two or more thereof. Suitable salts include sodium chloride, potassium chloride, magnesium chloride, calcium chloride, sodium lactate, sodium pyruvate, sodium ascorbate and mixtures of two or more thereof. Suitable sugars include dextrose, sucrose, fructose, xylose, mannose and mixtures of two or more thereof. Suitable sugar alcohols include sorbitol, mannitol, xylitol, maltitol, sorbitan and mixtures of two or more thereof. Suitable glycols include glycerol, propylene glycol and mixtures thereof. Suitable carbamides include urea. One or more of each type of tonicity agent may be present in the composition. Additionally or alternatively mixtures of different types of tonicity agents may be present in the composition.

In some embodiments the tonicity agent will be present in an amount to make the composition (preferably a solution or liquid) hypertonic. A hypertonic solution has an osmotic pressure greater than that of an isotonic solution. Typically when an hypertonic composition is added to the eye water is drawn from it. This may cause stinging, which is some cases should be avoided.

A hypotonic composition, preferably a solution, has an osmotic pressure lower that than of an isotonic composition (preferably a solution or liquid). Typically hypotonic ophthalmic compositions (preferably solutions or liquids) cause less irritation than hypertonic ones.

The composition may be chosen to be substantially isotonic, for example with human and/or animal tears. An isotonic composition (preferably solution or liquid) has an osmotic pressure substantially equal, (preferably equal) to that on the other side of a semipermeable membrane. For example, sodium chloride 0.9% is typically considered to be approximately isotonic with human tears. The osmolality of 0.9% w/w NaCl is 290 mOsm/kg. This is isotonic with blood and most cells in the human body.

Preferably, the compositions described herein are approximately isotonic.

Preferably, the composition (preferably in the form of a solution or liquid) has an osmolality of from 200 to 600 mOsm/kg, more preferably in the range 240 to 400 mOsm/kg, even more preferably in the range 280 to 320 mOsm/kg.

The osmolality of the composition may be varied by adjusting the amount tonicity agents present in the composition.

Osmolality may be determined by freezing point depression using a suitable automated device such as Advanced Instruments Inc Model 3320 Osmometer.

As outlined above, the composition of the present invention may further comprise one or more gelling agent(s) and/or a rheology modifying agent(s), such as viscosity modifier(s), and mixtures of two or more thereof.

The gelling agent may be pH sensitive (such as Carbomers) or thermally sensitive (such as polyethylene glycols or poly(N-isopropylacrylamide). The gelling agent may comprise one or more polysaccharides (such as carrageenans, glycosaminoglycans or starches). The gelling agent may comprise one or more cellulose or water soluble cellulose derivatives. The gelling agent may comprise one or more clays.

The gelling agent may, for example, be selected from guar gum, locust bean gum, xanthan gum, gum acacia, cellulose or water soluble cellulose derivatives (such as hydroxymethyl-cellulose hydroxyethylcellulose, hydroxypropyl-cellulose, carboxymethylcellulose or their salts), glycosaminoglycans (such as hyaluronic acid), clays (such as bentonites), magnesium aluminium silicates, "Carbomers" (salts of cross-linked polymers of acrylic acid), or glyceryl polymethacrylates or their dispersions in glycols. It will be understood that other suitable gelling agents may be used. Additionally, the inventors have discovered that some of the gelling agents (for example, carbomers) may also function as a chemical buffering agents thus preventing unwanted variation in the pH of the composition during storage and use.

Preferably, the composition of the present invention comprises from 0.01 to 1.0% by weight of a gelling agent, preferably from 0.02 to 0.5% by weight and more preferably from 0.05 to 0.25% by weight of the total composition.

It will be understood that the inclusion of these additives will be at the levels and with the type of materials which are found to be effective and useful.

In another aspect, the present invention provides methods for the treatment of eye diseases and conditions, in particular eye diseases and conditions that affect the surface of the eye, such as inflammatory conditions. Such methods generally comprise a step of: topically administering to a subject's eye surface, an effective amount of a composition of the invention.

According to an embodiment, the ophthalmic composition described herein is preserved. According to another embodiment, the ophthalmic composition described herein of the invention is unpreserved.

According to an embodiment, the ophthalmic composition of the present invention is presented in single use units.

According to another embodiment, the ophthalmic composition of the present invention is marketed in multidose containers.

This invention also relates to a medicament comprising the ophthalmic composition as described herein.

The ophthalmic composition may be a cosmetic composition and/or it may be for cosmetic use.

Preferably the ophthalmic composition as described herein has a viscosity of from 1 to 50 Pas, more preferably from 10 to 40 Pas. The viscosity may be determined using a cone-and-plate Rheometer at a shear rate of 1/s at a temperature of 37° C. An example of a suitable cone-and-plate Rheometer for measuring the viscosity of the composition is the Bohlin CVO 120. Preferably, the viscosity of the composition is such that it can easily be administered by topical application (for example via a dropper) to the eye.

Preferably the mean diameter of the droplets of aphrons are from 0.5 to 50 µm, more preferably in the range of from 1 to 20 µm, more preferably in the range of from 2 to 10 µm.

The mean diameter of the droplets (or aphrons) may be determined using Fraunhofer diffraction laser light scattering (for example Malvern Mastersizer 2000) or by optical microscopy.

The volume mean droplet size of the discontinuous phase droplets (preferably oil droplets) is preferably less than 60 µm, more preferably below 50 µm and most preferably below 40 µm. The volume mean droplet (or aphrons) size may be 20 determined using Fraunhofer diffraction laser light scattering (for example Malvern MASTERSIZER 2000) or by optical microscopy.

Structural integrity of a polyaphron dispersion and/or of a 25 polyaphron dispersion in a composition or product may be assessed using a droplet size distribution analyser, such as a Malvern MASTERSIZER Analyser, which determines particle size distribution via small angle laser diffraction.

In one aspect of the present invention there is provided an ophthalmic composition as described herein for use in the treatment of the human and/or animal eye by topical application.

In one embodiment, the ophthalmic composition as described herein may be for use in the treatment of glaucoma, dry eye, allergic conjunctivitis, bacterial infections, chalazion, styes, ocular inflammation, blepharitis, Behcet's disease, uveitis and mixtures of two or more thereof, for example by topical application.

In another embodiment, the ophthalmic composition as described herein may be for the manufacture of a medicament for the treatment of glaucoma, dry eye, allergic conjunctivitis, bacterial infections, chalazion, styes, ocular inflammation, blepharitis, Behcet's disease, uveitis and mixtures of two or more thereof, for example by topical application.

The ophthalmic composition as described herein may be in the form of an eye drop and/or gel for application to the eye. The ophthalmic composition may be a liquid or a solution.

Preferably the viscosity of the liquid is less than 1 Pa·s measured at 25° C., preferably at a shear rate of greater than 300 s$^{-1}$. Preferably the liquid is able to flow and take the shape of a container.

The ophthalmic composition may be used as an eye bath solution or liquid. The ophthalmic composition may be in the form of a dilutable solution or liquid.

In one embodiment the composition is in the form of a gel, which after application to the eye and during the blinking of the eyelid, at least a portion of the gel is liquefied. The liquefied composition may then be distributed, preferably evenly across the eye.

The composition as described herein preferably does not comprise a moulded body of a polymer matrix, such as those described in WO 2009/001099. Preferably, the ophthalmic composition as described herein is not capable of being moulded, preferably by sol-gel transition, into a desired shape. Instead, preferably the composition is in the form of a liquid, preferably a free-flowing liquid. Preferably it is not capable of undergoing a sol-gel transition. Preferably the composition as described herein is not in the form, or for use, in an eye patch. As will be understood by the person skilled in the art, an eye patch is a small patch that is worn in front of an eye. The composition as described herein is preferably for use in direct contact with one or more components of the eye, it is not designed for use on the eyelid, as an eye patch is designed. The compositions described in WO 2009/001099 behave as viscoelastic solids with a high degree of viscoelasticity, fracturing rather than flowing when deformed by applied stresses. Therefore the formulations described in WO 2009/001099 would not flow and spread on the eye. Thus, the formulations described in WO 2009/001099 are not suitable for application into the eye. Instead, they would only be suitable for use in eye patches over the eye, preformed and not flowing in use.

In contrast to this, in the present invention, the composition is preferably designed such that upon application of the composition to the eye the polyaphron droplets flow and spread across the eye at the shear stress experienced in the eye (such as through blinking). This is because these formulations are preferably highly shear thinning, preferably viscoelastic liquids. The shear rate in the eye during blinking is estimated to be approximately between 300 and 500 $s^{-1}$. Preferably the viscosity of the composition is less than 1 Pa·s measured at 25° C., preferably at a shear rate of greater than 300 $s^{-1}$.

In one embodiment of present invention there is provided an ophthalmic composition as described herein for use in the manufacture of a medicament for the treatment of an eye condition, for example of dry eye or severe dry eye.

It will be understood that the ophthalmic composition as described herein is suitable for application to the human and/or animal eye. Preferably the composition is sterile and/or aseptic.

According to one aspect of the present invention there is provided a method of making the ophthalmic composition as described herein comprising the following steps:
(i) providing a hydrophilic solvent;
(ii) providing a hydrophobic solvent;
(iii) mixing the hydrophilic solvent with the hydrophobic solvent under suitable conditions to form the composition comprising a polyaphron dispersion;
wherein the hydrophilic solvent and/or the hydrophobic solvent comprises a surfactant.

The ophthalmic composition may be prepared under sterile and/or aseptic conditions. The ophthalmic composition may be autoclaved to sterilise it. The ophthalmic composition may be exposed to gamma radiation to sterilise it.

Typically to autoclave a composition it will be subjected to high pressure saturated steam (for example at a pressure of approximately 100 kPa) at approximately 110 to 140° C., or from 120 to 135° C. for approximately 10 to 20 minutes. Suitable conditions may be sterilizing the composition after manufacture in autoclaves for approximately 15 minutes at 121° C. Suitable conditions will depend on the loading and the contents. An example of a suitable autoclaving machine is Prestige Model 21004 Portable Autoclave or Prestige Optima B Class Autoclave.

The present inventors have surprisingly found that polyaphron dispersions are substantially robust to autoclaving. In other words, the polyaphrons dispersions substantially maintain their physical integrity during and after autoclaving. In contrast to this, it has been found that emulsions are typically adversely affected by autoclaving. Without wishing to be bound by any particular theory, it is thought that this difference is a result of the different interactions of surfactants in emulsions and polyaphron dispersions with respect to the continuous and discontinuous phases. It is thought that in emulsions the nature of the surfactant interaction with the continuous and discontinuous phases is much more sensitive to changes (and in particular increases) in temperature. Autoclaving may be carried out at high temperatures, for example at temperatures above 110° C., above 120° C., or above 130° C. Typically autoclaving is carried out at 121° C. or 126° C. Under these conditions emulsions are likely to become unstable and the emulsion may separate (or start to separate) into hydrophobic and hydrophilic layers. In contrast to this, in polyaphron dispersions the surfactants are more closely and robustly associated with the discontinuous phases of the dispersions. It is thought for this reason that typically polyaphrons dispersions are much more physically stable, and less likely to separate into distinct phases than emulsions. It is particularly advantageous to be able to autoclave the compositions as it will be understood that compositions for administration to the eye should be sterile to avoid infection. One advantageous of autoclaving the composition is that preservatives may be omitted from the composition and/or the amount of preservative required may be reduced.

Advantageously, it has also surprisingly been found that after autoclaving the mean diameter of the droplets of aphrons has varied by less than 10%, preferably less than 5%, more preferably less than 2%.

As outlined above, preservatives may be added to the composition. It is particularly advantageous to add preservatives if autoclaving is not used. The preservative(s) is (are) added to keep the composition, which is typically prepared under sterile conditions, in suitable state for use and prevent, for example, bacterial growth. The inventors have surprisingly found that using polyaphron dispersions rather than emulsions enables lower levels of preservatives to be used. In order for emulsions to remain stable it is necessary for higher levels of surfactants to be present than in an equivalent polyaphron dispersion. The inventors have found that when higher levels of surfactant are required, higher levels of preservatives are required to maintain the same antibacterial effect. It is advantageous to use lower levels of preservatives, whilst still preserving the composition, for a number of reasons: For example, to reduce cost of preparing the composition; to reduce risks of irritation caused by the preservatives upon application of the composition to the eye; and/or to reduce the risk of undesirable interaction of the preservative with any active agents or components of the composition.

Optionally the hydrophilic solvent and/or the hydrophobic solvent comprises one or more pharmaceutically active agents.

Suitable methods for preparing polyaphron dispersions are described in U.S. Pat. No. 4,486,333 and EP 1469940. It will be understood by those skilled in the art that other manufacturing methods may be used, as appropriate.

Surprisingly, the present inventors have found that by using the method of preparing polyaphron dispersions as described herein and as outlined in EP 1469940 is advantageous over methods of making polyaphrons dispersions by foaming methods, such as those previously described by Sebba (for example those described in U.S. Pat. No. 4,486,333). Using foaming methods such as those described in Sebba can generate unstable formulations. Without wishing to be bound by any particular theory, it is believed that this is related to the droplet size distribution prepared using the foaming methods. Preferably, the polyaphron dispersion is formed without forming a gas-foam intermediate.

Accordingly to another aspect of the present invention, there is provided a method of making the ophthalmic composition as described herein comprising the following steps:
preparing a first polyaphron dispersion optionally comprising a pharmaceutically active agent;
preparing a second polyaphron dispersion optionally comprising a pharmaceutically active agent;
and mixing together said first and second polyaphron dispersions to form the composition.

The method may further comprise:
preparing a third or further polyaphron dispersion optionally comprising additives such as inert diluents, buffering agents, dispersing or wetting agents, preservatives, chelating agents, anti-foaming agents, antioxidants, gelling agents, permeation enhancers, tonicity agents and combinations of one or more thereof;

and mixing said third or further polyaphron with said first and second polyaphron dispersions to form the composition.

Additives such as inert diluents, buffering agents, dispersing or wetting agents, gelling agents, preservatives, chelating agents, anti-foaming agents, antioxidants, gelling agents, permeation enhancers, tonicity agents and combinations of one or more thereof may be added to either or both of the hydrophilic solvent and/or the hydrophobic solvent before the polyaphron dispersion is formed. Additionally, and/or alternatively additives such as inert diluents, buffering agents, dispersing or wetting agents, gelling agents, preservatives, chelating agents, anti-foaming agents, antioxidants, permeation enhancers, gelling agents, tonicity agents and combinations of one or more thereof may be added to the composition after polyaphron formation.

The ophthalmic composition may comprise more than one polyaphron dispersion. Each polyaphron dispersion may be composed of one or more different materials to the other polyaphron dispersions in the ophthalmic composition. Each of the polyaphron dispersions may comprise the same or a different pharmaceutically active agent (preferably in the discontinuous phase of the polyaphron dispersion).

According to one embodiment of the present invention there is provided a method of making the ophthalmic composition as described herein comprising the following steps: (i) providing a polyaphron dispersion and (i) mixing said polyaphron dispersion with a pharmaceutically active agent. Preferably the pharmaceutically active agent is dissolved and/or at least partially solubilised in a solvent. Preferably the pharmaceutically active agent is dissolved and/or at least partially solubilised in a hydrophilic solvent.

According to another embodiment of the present invention there is provided a method of making the ophthalmic composition as described herein comprising the following steps: (i) at least partially dispersing and/or dissolving a pharmaceutically active agent in a hydrophobic solvent; (ii) mixing said hydrophobic solvent comprising said pharmaceutically active agent with at least one hydrophilic solvent and at least one surfactant under suitable conditions to form a polyaphron dispersion.

As outlined above, it will be understood that the ophthalmic composition as described herein is suitable for application to the human and/or animal eye. Typically this means that the composition is sterile and/or aseptic.

The ophthalmic composition as described herein may be prepared under sterile and/or aseptic conditions so that the ophthalmic composition produced is sterile and/or aseptic. Additionally and/or alternatively, the ophthalmic composition may be formed in sterile and/or aseptic and/or non-sterile and/or non-aseptic conditions and then subsequently treated to produce a sterile and/or aseptic product. Preferably the method of making ophthalmic composition as described herein further comprises autoclaving the ophthalmic composition. In particular, the present inventors have found that the ophthalmic composition as described herein comprising the polyaphron dispersion(s) may be autoclaved under suitable conditions to form a composition suitable for administration to the human and/or animal eye. Suitable autoclaving conditions are known to the person skilled in the art. Typically, autoclaving is carried out at approximately 121° C.

In one aspect of the present invention there is provided the ophthalmic composition as described herein for use as a medicament. In particular there is provided the ophthalmic composition as described herein for use in the prophylactic or therapeutic treatment of a human and/or animal eye.

In one aspect of the present invention there is provided a device for dropwise dispensing of a composition, the device comprising a container holding the composition as described herein.

In one embodiment of the present invention there is provided the method of treating the eye of a human and/or animal, the method comprising administering the ophthalmic composition described herein to the eye. The ophthalmic composition may be administered dropwise to the eye. It may be administered using a dropper or it may be poured into the eye.

In a preferred embodiment, the ophthalmic composition comprises a polyaphron dispersion, a pharmaceutically active agent and cationic surfactant. Preferably, it also contains a buffering agent and/or an inert diluent.

In another preferred embodiment, the ophthalmic composition comprises a polyaphron dispersion, a pharmaceutically active agent and non-ionic surfactant. Preferably, it also contains a buffering agent and/or an inert diluent.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

The terms "approximately" and "about", as used herein in reference to a number, generally includes numbers that fall within a range of 10% in either direction of the number (greater than or less than the number) unless otherwise stated or otherwise evident from the context (except where such a number would exceed a possible value).

The foregoing detailed description has been provided by way of explanation and illustration, and is not intended to limit the scope of the appended claims. Many variations in the presently preferred embodiments illustrated herein will be apparent to one of ordinary skill in the art, and remain within the scope of the appended claims and their equivalents.

The present invention will now be described further, by way of example only, with reference to the following figures, in which:

FIG. 1 is a graph showing apparent viscosity (Pa·s) against shear rate ($s^{-1}$) of the composition described in Example 3.

The following non-limiting examples further illustrate the present invention.

EXAMPLES

Example 1

Gel Polyaphron Dispersion of the Following Composition was Prepared by the Following Method

| Gel POLYAPHRON DISPERSION | |
|---|---|
| | % |
| Oil Phase | |
| Cyclosporin A solution* (2.5%) in Caprylic/Capric Triglyceride (MIGLYOL 812 - Condea) | 89.10 |
| Laureth-4 (VOLPO L4 - Croda) | 0.90 |
| Aqueous Phase | |
| Poloxamer 188 (PLURONIC F68 - BASF) | 0.50 |
| Demineralised Water | 9.50 |

-continued

| Gel POLYAPHRON DISPERSION | |
|---|---|
| FINAL PRODUCT | % w/w |
| GEL POLYAPHRON DISPERSION | 2.24 |
| 0.2% Polyacrylic acid (Carbomer 980, Noveon) | 95.56 |
| Glycerin | 2.20 |
| NaOH, to pH 7.0 to 7.4 | qs |

*The cyclosporin A content in the final formulation is 500 µg/g. The osmolality of the final product is in the range 250-320 mOsm/kg.

Manufacturing Method

The polyaphron dispersion was made by the following method:

A low form, 250 ml laboratory beaker (internal diameter 6.5 cm) was charged with sufficient aqueous (continuous) phase to make 30 g of gel polyaphron. This was stirred at 200 rpm with a four-bladed impeller having a diameter of 6.0 cm whilst adding the oil (discontinuous) phase drop wise from a Pasteur pipette. The rate of addition at the start of the process was slow (approximately one drop every 7 seconds) but was speeded up once 10% of the oil phase had been added so that the total time to make the gel polyaphron was approximately 20 minutes.

Prior to the manufacture of the gel polyaphron dispersion, active was dissolved in the appropriate phase by gentle stirring overnight with a magnetic stirrer at room temperature in a covered beaker.

To form the final product, the polyaphron was mixed with the Carbomer gel and glycerine and the pH adjusted by the addition of NaOH solution (20% w/w) to the required pH.

Formulations were loaded into suitable vessels and sterilised by autoclave (121° C., 15 minutes).

Stability Measurements

Stability measurements made using the method outlined below.

The cyclosporin was extracted from the composition of Example 1 into acetonitrile and assayed by HPLC under the conditions given below.

HPLC Conditions:

Column: NOVA-PAK C8, 4 µm particle size, 3.9×150 mm column (Waters)

Mobile phase: 75% v/v acetonitrile, 25% v/v 5 mM $PO_4$ buffer, pH 5.1.

Flow rate: 1 ml/minute.

Column Temperature: 50° C.

Injection volume: 1 µl.

Detector wavelength: 205 nm.

Retention time for cyclosporin was 3.0 minutes

The inventors observed that after 3 months storage at 40° C., the levels of cyclosporin was 102%±3% of the original level.

Permeation of Cyclosporine Through Cornea

In order to determine the permeation of cyclosporine (CsA) formulations into and through the cornea, ex vivo studies were conducted. In brief, the corneas from rabbits were taken and mounted onto Ussing diffusion cells incubated at 37° C. and perfused with carbogen (95/5 oxygen/carbonic acid). Approximately 3 ml sample was placed in the donor side of the chamber, 3 ml Ringers solution (6.5 g NaCl, 0.42 g KCl, 0.25 g $CaCl_2$ and 1 mole of Sodium bicarbonate per litre; isotonic solution pH 7.2) was placed in the receptor side of the chamber.

Permeation across the cornea was determined by collecting 200 µl receptor phase at the appropriate time points. At time zero and at 8 hours (termination of the experiment) 100 µl of sample from the donor phase was taken for analysis. Corneas were collected and split into the stomal and epithelial parts. The cyclosporine in the cornea sections were analysed after extraction into 50/50 methanol/water. Levels of CsA in the receptor chamber, the cornea and in the donor chamber were determined by HPLC analysis. Formulations used were based on Example 1. The table below summarises the changes made to this formulation.

FN# Summary

1 As Example 1

2 As example 1 with the addition of 1% w/w TWEEN 20 (polyoxyethylene (20) sorbitan monolaurate)

3 No Carbomer, 0.01% benzalkonium chloride (BAC)

4 Castor oil replaces medium chain triglyceride

5 As example 1 with the addition of 1% BRIJ 58 (polyoxyethylene (20) cetyl ether)

Alternative Representation of Formulae:

| Ingredient | FN1 | FN2 | FN3 | FN4 | FN5 |
|---|---|---|---|---|---|
| Cyclosporine | 0.05% | 0.05% | 0.05% | 0.05% | 0.05% |
| MCT | 1.95% | 1.95% | 1.95% | — | 1.95% |
| Castor oil | — | — | — | 0.95% | — |
| Carbomer 980 | 0.10% | 0.10% | — | 0.10% | 0.10% |
| Glycerol | 2.40% | 2.40% | 2.40% | 2.40% | 2.40% |
| Poloxamer 188 | 0.01% | 0.01% | 0.01% | — | 0.01% |
| TWEEN 80 | — | — | — | 0.01% | — |
| Laurette 4 | 0.02% | 0.02% | 0.02% | 0.01% | 0.02% |
| TWEEN 20 | — | 1.00% | — | — | — |
| BAC* | — | — | 0.03% | — | — |
| BRIJ 58 | — | — | — | — | 1.00% |
| Water | 95.47% | 94.47% | 94.54% | 96.48% | 94.47% |
| NaOH | qs to pH 6.5 to 7.0 | | | | |

*benzalkonium chloride

Results

Total amount of CsA (cyclosporine A) found in the cornea and passed through the cornea into the receptor chamber are summarised below.

| | CsA level | total amount after 8 h (µg) | | percent of initial after 8 h | | |
|---|---|---|---|---|---|---|
| FN | (µg/g) | Cornea | Receptor | Donor | Cornea | Receptor |
| 1 | 421 | 45.6 | 0.004 | 31.2% | 3.6% | 0.0003% |
| 2 | 531 | 37.4 | 0.004 | 49.6% | 2.3% | 0.0003% |
| 3 | 445 | 43.1 | 0.011 | 26.9% | 3.2% | 0.0008% |
| 4 | 530 | 25.5 | —** | 15.1% | 1.6% | — |
| 5 | 536 | 100.0 | 0.012 | 80.7% | 6.2% | 0.0007% |

**Flux could not be correlated with time so no data presented

From these data the following conclusions may be made:

1. The presence of Brij 58 at 1% had a significant positive effect on the permeation of CsA into the cornea.
2. Less good permeation results from the use of castor oil as the vehicle for the lipophilic CsA were observed.
3. The use of Tween 20 has a slight detrimental effect on the permeation of CsA into and through the cornea.
4. The presence of benzalkonium chloride has no significant effect on permeation of CsA.

Example 2

Gel Polyaphron Dispersion of the Following Composition was Prepared by the Following Method

| Gel POLYAPHRON DISPERSION | |
|---|---|
| | % |
| Oil Phase | |
| Flurbiprofen solution* (7.0%) in castor oil (Fluka) | 89.10 |
| Laureth-4 (VOLPO L4 - Croda) | 0.90 |
| Aqueous Phase | |
| Poloxamer 188 (PLURONIC F68 - BASF) | 0.50 |
| Demineralised Water | 9.50 |

| FINAL PRODUCT | % w/w |
|---|---|
| GEL POLYAPHRON DISPERSION | 0.48 |
| 0.2% Polyacrylic acid (Carbomer 980, Noveon) | 95.32 |
| Sorbitol (Sigma) | 4.20 |
| NaOH, to pH 7.0 | qs |

*The flurbiprofen content in the final formulation is 300 µg/g. The osmolality of the final product is in the range 250-320 mOsm/kg.

Manufacturing Method

The method used was precisely as described for Example 1.

Stability Measurements

Stability measurements made using the method outlined below.

The flurbiprofen was extracted from the composition of Example 1 into acetonitrile and assayed by HPLC under the conditions given below.

HPLC Conditions:

Column: NOVA-PAK C18, 5 µm particle size, 3.9×100 mm column (Waters)

Mobile phase: 65% v/v acetonitrile, 35% v/v 0.1M sodium acetate, pH 6.3.

Flow rate: 1 ml/minute.

Column Temperature: 25° C.

Injection volume: 25 µl.

Detector wavelength: 248 nm.

Retention time for flurbiprofen was 4.5 minutes

The inventors observed that after 3 months storage at 40° C., the levels of flurbiprofen were 98%±2% of the original level.

Example 3

Gel Polyaphron Dispersion of the Following Composition was Prepared by the Following Method

| Gel POLYAPHRON DISPERSION | |
|---|---|
| | % |
| Oil Phase | |
| Latanoprost solution* (0.28%) in Caprylic/Capric Triglyceride (MYGLIOL 812 - Condea) | 89.10 |
| Laureth-4 (VOLPO L4 - Croda) | 0.90 |
| Aqueous Phase | |
| Poloxamer 188 (PLURONIC F68 - BASF) | 0.50 |
| Demineralised Water | 9.50 |

| FINAL PRODUCT | % w/w |
|---|---|
| GEL POLYAPHRON DISPERSION | 2.00 |
| 0.1% Polyacrylic acid (Carbomer 980) | 93.10 |
| Sorbitol (CxPharmsorboidex P, S Black) | 4.90 |
| NaOH, to pH 6.7 | qs |

*The latanoprost content in the final formulation is 50.0 µg/g. The osmolality of the final product is in the range 250-320 mOsm/kg.

Manufacturing Method

The polyaphron dispersion was made by the following method:

A low form, 250 ml laboratory beaker (internal diameter 6.5 cm) was charged with sufficient aqueous (continuous) phase to make 30 g of gel polyaphron. This was stirred at 200 rpm with a four-bladed impeller having a diameter of 6.0 cm whilst adding the oil (discontinuous) phase drop wise from a Pasteur pipette. The rate of addition at the start of the process was slow (approximately one drop every 7 seconds) but was speeded up once 10% of the oil phase had been added so that the total time to make the gel polyaphron was approximately 20 minutes.

Prior to the manufacture of the gel polyaphron dispersion, the active, a liquid at room temperature, was mixed with the appropriate phase by gentle stirring with a magnetic stirrer at room temperature in a covered beaker. Dispersion of the active into the oil phase took less than 30 minutes.

To form the final product, the polyaphron was mixed with the Carbomer gel and glycerine and the pH adjusted by the addition of NaOH solution (20% w/w) to the required pH.

Stability Measurements

Stability measurements made using the method outlined below.

The latanoprost was extracted from the composition of Example 3 into acetonitrile and assayed by HPLC under the conditions given below.

HPLC Conditions:

Instrument: Acquity H Class (Waters)

Column: BEH C18, 1.7 µm particle size, 2.1×50 mm column (Waters) with VanGuard C18 guard column (Waters)

Mobile phase: 70% v/v acetonitrile, 30% v/v water.

Flow rate: 0.5 ml/minute.

Column Temperature: 40° C.

Injection volume: 10 µl.

Detector wavelength: 210 nm.

Retention time for latanoprost was 0.4 minutes

Formulation was dispensed into autoclavable eyedropper bottles and sterilised using a standard run in a Prestige Autoclave, holding samples at 121° C. for 15 minutes. Autoclavation cycle was confirmed using indicator tape.

The inventors observed that after autoclaving the formulation, the levels of latanoprost was 99.4%±0.1% of the level in the untreated sample.

Shear Experiment

Comparison of apparent viscosity against shear rate for a carbomer-stabilised eyedrop formulation (using Example 3). The shear rate range covered was from 0.1 to 500/s. The same sample was subjected to the same shear rate regime after 5 minutes rest. The results are shown in FIG. 1. There is no significant difference between the two viscosity profiles, indicating that high shear does not permanently affect the structure of this formulation.

Method

Rheology measurements were carried out using the Bohlin CVO 120 rheometer. Controlled shear rates were applied to a sample (approx 2 g) via a 40 mm diameter stainless steel cone and plate geometry. Cone angle=4°, temperature maintained at 25° C. The shear stress required to reach the required shear rate was controlled directly by the instrument. Apparent viscosity ($\eta$) is related to shear rate ($\gamma$) and shear stress ($\tau$) by the equation $\eta=\tau/\gamma$.

Example 4

Gel Polyaphron Dispersion of the Following Composition was Prepared by the Following Method

| Gel POLYAPHRON DISPERSION | |
| --- | --- |
| | % |
| Oil Phase | |
| Latanoprost solution* (0.28%) in Caprylic/ Capric Triglyceride (MYGLIOL 812 - Condea) | 89.10 |
| Laureth-4 (VOLPO L4 - Croda) | 0.90 |
| Aqueous Phase | |
| Poloxamer 188 (PLURONIC F68 - BASF) | 0.50 |
| Demineralised Water | 9.50 |
| FINAL PRODUCT | % w/w |
| GEL POLYAPHRON DISPERSION | 2.00 |
| 0.1% Polyacrylic acid (Carbomer 980) | 93.10 |
| Dextrose (D-glucose anhydrous, Fisher) | 4.90 |
| NaOH, to pH 6.7 | qs |

*The latanoprost content in the final formulation is 50.0 µg/g. The osmolality of the final product is in the range 250-320 mOsm/kg.

Manufacturing Method

The polyaphron dispersion was made as in Example 3.

Stability Measurements

Stability measurements made using the method outlined below.

The latanoprost was extracted from the composition of Example 4 into acetonitrile and assayed by HPLC under the conditions given for Example 3.

Formulation was dispensed into autoclavable eyedropper bottles and sterilised using a standard run in a Prestige Autoclave, holding samples at 121° C. for 15 minutes. Autoclavation cycle was confirmed using indicator tape.

The inventors observed that after autoclaving the formulation, the levels of latanoprost was 83.7%±0.4% of the level in the untreated sample.

In this example the use of dextrose to adjust the osmolality of the formulation resulted in an unstable formulation, in contrast to Example 3.

Example 5

Gel Polyaphron Dispersion of the Following Composition was Prepared by the Following Method

| Gel POLYAPHRON DISPERSION | |
| --- | --- |
| | % |
| Oil Phase | |
| Fluticasone solution* (0.28%) in Caprylic/ Capric Triglyceride (MYGLIOL 812 - Condea) | 89.10 |
| Laureth-4 (VOLPO L4 - Croda) | 0.90 |
| Aqueous Phase | |
| Poloxamer 188 (PLURONIC F68 - BASF) | 0.50 |
| Demineralised Water | 9.50 |
| FINAL PRODUCT | % w/w |
| GEL POLYAPHRON DISPERSION | 2.00 |
| 0.1% Polyacrylic acid (Carbomer 980) | 93.05 |
| Polyoxyethylene (20) stearyl ether (Acros) | 0.05 |
| Sorbitol (CxPharmsorboidex P, S Black) | 4.90 |
| NaOH, to pH 6.7 | qs |

*The fluticasone content in the final formulation is 50 µg/g. The osmolality of the final product is in the range 250-320 mOsm/kg.

Manufacturing Method

The polyaphron dispersion was made by the following method:

A low form, 250 ml laboratory beaker (internal diameter 6.5 cm) was charged with sufficient aqueous (continuous) phase to make 30 g of gel polyaphron. This was stirred at 200 rpm with a four-bladed impeller having a diameter of 6.0 cm whilst adding the oil (discontinuous) phase drop wise from a Pasteur pipette. The rate of addition at the start of the process was slow (approximately one drop every 7 seconds) but was speeded up once 10% of the oil phase had been added so that the total time to make the gel polyaphron was approximately 20 minutes.

Prior to the manufacture of the gel polyaphron dispersion, the active was dissolved in the appropriate phase by gentle stirring with a magnetic stirrer at room temperature in a covered beaker. Dissolution of the active into the oil phase took approximately 2 hours.

To form the final product, the polyaphron was mixed with the Carbomer gel and glycerine and the pH adjusted by the addition of NaOH solution (20% w/w) to the required pH.

Formulation was dispensed into autoclavable eyedropper bottles and sterilised using a standard run in a Prestige Autoclave, holding samples at 121° C. for 15 minutes. Autoclavation cycle was confirmed using indicator tape.

Example 6

Gel Polyaphron Dispersion of the Following Composition was Prepared by the Following Method

| Gel POLYAPHRON DISPERSION | |
| --- | --- |
| | % |
| Oil Phase | |
| Vancomycin solution* (0.168%) in Caprylic/ Capric Triglyceride (MYGLIOL 812 - Condea) | 89.10 |
| Sorbitan monooleate (SPAN 80, Sigma) | 0.90 |
| Aqueous Phase | |
| Poloxamer 188 (PLURONIC F68 - BASF) | 0.50 |
| Demineralised Water | 9.50 |
| FINAL PRODUCT | % w/w |
| GEL POLYAPHRON DISPERSION | 2.00 |
| 0.1% Polyacrylic acid (Carbomer 980) | 95.50 |

-continued

| Gel POLYAPHRON DISPERSION | |
|---|---|
| Glycerol (Fisher) | 2.50 |
| NaOH, to pH 6.7 | qs |

*The vancomycin content in the final formulation is 30 μg/g. The osmolality of the final product is in the range 250-320 mOsm/kg.

Manufacturing Method

The polyaphron dispersion was made as in Example 3.

Example 7

Gel Polyaphron Dispersion of the Following Composition was Prepared by the Following Method

| Gel POLYAPHRON DISPERSION | |
|---|---|
| | % |
| Oil Phase | |
| Cyclosporin A solution* (2.5%) in Caprylic/Capric Triglyceride (MYGLIOL 812 - Condea) | 89.10 |
| Laureth-4 (VOLPO L4 - Croda) | 0.90 |
| Aqueous Phase | |
| Poloxamer 188 (PLURONIC F68 - BASF) | 0.50 |
| Demineralised Water | 9.50 |

| FINAL PRODUCT | % w/w |
|---|---|
| GEL POLYAPHRON DISPERSION | 2.24 |
| 0.2% xanthan gum (Aldrich) | 95.56 |
| Glycerin | 2.20 |
| NaCl | 0.10 |
| NaOH, to pH 7.0 to 7.4 | qs |

*The cyclosporin A content in the final formulation is 500 μg/g. The osmolality of the final product is in the range 250-320 mOsm/kg.

Manufacturing Method

The polyaphron dispersion was made by the following method:

A low form, 250 ml laboratory beaker (internal diameter 6.5 cm) was charged with sufficient aqueous (continuous) phase to make 30 g of gel polyaphron. This was stirred at 200 rpm with a four-bladed impeller having a diameter of 6.0 cm whilst adding the oil (discontinuous) phase drop wise from a Pasteur pipette. The rate of addition at the start of the process was slow (approximately one drop every 7 seconds) but was speeded up once 10% of the oil phase had been added so that the total time to make the gel polyaphron was approximately 20 minutes.

Prior to the manufacture of the gel polyaphron dispersion, active was dissolved in the appropriate phase by gentle stirring overnight with a magnetic stirrer at room temperature in a covered beaker.

To form the final product, the polyaphron was dispersed in the water. Sodium Chloride was added as a solution. The required amount of xanthan gum was dispersed in the glycerol before adding to the diluted polyaphon. The pH of the formulation was adjusted with either NaOH or HCl to ph 6.50 to 7.00.

Formulations were loaded into suitable vessels and sterilised by autoclave (121° C., 15 minutes).

Example 8

Gel Polyaphron Dispersion of the Following Composition was Prepared by the Following Method

| Gel POLYAPHRON DISPERSION | |
|---|---|
| | % |
| Oil Phase | |
| Ketotifen solution* (0.255 %) in soybean oil (Aldrich) | 89.10 |
| Laureth-4 (VOLPO L4 - Croda) | 0.90 |
| Aqueous Phase | |
| Polysorbate 80 (TWEEN 80, Sigma) | 0.50 |
| Demineralised Water | 9.50 |

| FINAL PRODUCT | % w/w |
|---|---|
| GEL POLYAPHRON DISPERSION | 1.10 |
| 0.1% Polyacrylic acid (Carbomer 980) | 93.05 |
| Polyoxyethylene (20) stearyl ether (Acros) | 0.05 |
| Sorbitol (CxPharmsorboidex P, S Black) | 4.90 |
| NaOH, to pH 6.7 | qs |

*The ketotifen content in the final formulation is 250 μg/g. The osmolality of the final product is in the range 250-320 mOsm/kg.

Manufacturing Method

The polyaphron dispersion was made by the method described in Example 1.

To form the final product, the polyaphron was mixed with the Carbomer gel and glycerine and the pH adjusted by the addition of NaOH solution (20% w/w) to the required pH.

Formulations were loaded into suitable vessels and sterilised by autoclave (121° C., 15 minutes).

Example 9

Gel Polyaphron Dispersion of the Following Composition was Prepared by the Following Method

| Gel POLYAPHRON DISPERSION | |
|---|---|
| | % |
| Oil Phase | |
| Propranolol solution* (5.10%) in Caprylic/Capric Triglyceride (MYGLIOL 812 - Condea) | 89.10 |
| Laureth-4 (VOLPO L4 - Croda) | 0.90 |
| Aqueous Phase | |
| Poloxamer 188 (PLURONIC F68 - BASF) | 0.50 |
| Demineralised Water | 9.50 |

| FINAL PRODUCT | % w/w |
|---|---|
| GEL POLYAPHRON DISPERSION | 5.50 |
| 0.1% xanthan gum, 0.1% locust bean gum (both Aldrich) | 92.00 |
| Glycerol (Fisher) | 2.50 |
| NaOH, to pH 6.7 | qs |

*The propranolol contentin the final formulation is 2.5 μg/g. The osmolalityof the final product is in the range 250-320 mOsm/kg.

Manufacturing Method

The polyaphron dispersion was made as in Example 1.

The polyaphron was dispersed into water by stirring at 260 rpm prior to the addition of the xanthan and locust bean gum. The gums were added as a slurry, predispersed in glycerol. Stirring was continued until the gel structure had formed, approximately 10 minutes.

Formulations were loaded into suitable vessels and sterilised by autoclave (121° C., 15 minutes).

Example 10

Gel Polyaphron Dispersion of the Following Composition was Prepared by the Following Method

| Gel POLYAPHRON DISPERSION | |
|---|---|
| | % |
| Oil Phase | |
| Clotrimazole solution* (2.5%) in Caprylic/Capric Triglyceride (MYGLIOL 812 - Condea) | 89.10 |
| Sorbitan monooleate (SPAN 80, Sigma) | 0.90 |
| Aqueous Phase | |
| Poloxamer 188 (PLURONIC F68 - BASF) | 0.50 |
| Demineralised Water | 9.50 |
| FINAL PRODUCT | % w/w |
| GEL POLYAPHRON DISPERSION | 4.50 |
| 0.2% Polyacrylic acid (Carbomer 980) | 90.60 |
| Sorbitol (CxPharmsorboidex P, S Black) | 4.90 |
| NaOH, to pH 7.0 to 7.4 | qs |

*The clotrimazole content in the final formulation is 1000 μg/g. The osmolarity of the final product is in the range 250-20 mOsm/kg.

Manufacturing Method

The polyaphron dispersion was made by the method described in Example 1.

Formulations were loaded into suitable vessels and sterilised by autoclave (121° C., 15 minutes).

The present invention will now be described in relation to the following non-limiting clauses:

1. An ophthalmic composition comprising a polyaphron dispersion.
2. The ophthalmic composition according to clause 1 comprising a pharmaceutically active agent.
3. The ophthalmic composition according to clause 2 wherein the pharmaceutically active agent is selected from antihistamines, betablockers, corticosteroids, prostaglandins, non-steroidal anti-inflammatory drugs (NSAIDs), immune modulators, anaesthetics, antibiotics, carbonic anhydrase inhibitors, vasoconstrictors, and mixtures of two or more thereof.
4. The ophthalmic composition according to any of the preceding clauses wherein the pharmaceutically active agent comprises cyclosporine.
5. The ophthalmic composition according to any of the preceding clauses comprising an omega-3 fatty acid.
6. The ophthalmic composition according to any of the preceding clauses wherein the composition has a pH of from 3.5 to 9, preferably from 5 to 8, more preferably from 6 to 7.5.
7. The ophthalmic composition according to any of the preceding clauses comprising a gelling agent.
8. The ophthalmic composition according to any one of the preceding clauses having a viscosity of 1 to 50 Pas.
9. The ophthalmic composition according to any of the preceding clauses comprising a surfactant selected from the group consisting of non-ionic surfactants, cationic surfactants, anionic surfactants, zwitterionic surfactants and mixtures of two or more thereof.
10. The ophthalmic composition according to any one of the preceding clauses comprising a pharmaceutically acceptable oil selected from the group consisting of castor oil, long chain triglycerides, medium chain triglycerides, mineral oil, silicones, phospholipids, mono- and diglycerides and mixtures of two or more thereof.
11. The ophthalmic composition according to any of the preceding clauses for use in the treatment of the human and/or animal eye by topical application.
12. The ophthalmic composition according to any of the preceding clauses in the form of an eye drop and/or gel for application to the eye.
13. The ophthalmic composition according any one of the preceding clauses wherein the mean diameter of the droplets of aphrons are from 0.5 to 50 μm.
14. A method of making the ophthalmic composition according to any of the preceding clauses comprising the following steps:
    (i) providing a hydrophilic solvent;
    (ii) providing a hydrophobic solvent;
    (iii) mixing the hydrophilic solvent with the hydrophobic solvent under suitable conditions to form the composition comprising a polyaphron dispersion;
    wherein the hydrophilic solvent and/or the hydrophobic solvent comprises a surfactant;
    and wherein the hydrophilic solvent and/or the hydrophobic solvent optionally comprises a pharmaceutically active agent.
15. The method according to clause 14 which is carried out under sterile and/or aseptic conditions.
16. The method according to clause 14 or 15 which further comprises autoclaving the ophthalmic composition.
17. A device for dropwise dispensing of a composition, the device comprising a container holding the composition as defined in any of the preceding clauses.

The invention claimed is:

1. An ophthalmic composition comprising:
    a polyaphron dispersion comprising a hydrophobic discontinuous phase, at least 85% of a hydrophilic continuous phase by weight of the composition, and less than 3% of surfactants by weight of the polyaphron dispersion, and cyclosporine;
    wherein the ophthalmic composition is a sterile and/or aseptic composition formulated in the form of an eye drop for administration to an eye, wherein the polyaphron dispersion remains intact when administered to the eye, and wherein the ophthalmic composition does not comprise a fluorinated surfactant.

2. The ophthalmic composition according to claim 1, wherein the composition is in the form of a liquid.

3. The ophthalmic composition according to claim 1, wherein the composition has an osmolality of from 200 to 600 mOsm/kg.

4. The ophthalmic composition according to claim 1 wherein the composition further comprises a tonicity agent selected from the group consisting of a sugar, a sugar alcohol, a glycol, a carbamide and mixtures of two or more thereof.

5. The ophthalmic composition according to claim 1, wherein the composition further comprises an omega-3 fatty acid.

6. The ophthalmic composition according to claim 1, wherein the composition has a pH of from 3.5 to 9.

7. The ophthalmic composition according to claim 1, wherein the composition further comprises a gelling agent.

8. The ophthalmic composition according to claim 1, wherein the composition has a viscosity of 1 to 50 Pas at a shear rate of $1\ s^{-1}$.

9. The ophthalmic composition according to claim 1, wherein the surfactant is selected from the group consisting of one or more non-ionic surfactant(s), cationic surfactant(s), anionic surfactant(s), zwitterionic surfactant(s) and mixtures of two or more thereof.

10. The ophthalmic composition according to claim 1, wherein the composition further comprises a pharmaceutically acceptable oil selected from the group consisting of castor oil, long chain triglycerides, medium chain triglycerides, mineral oil, silicones, phospholipids, mono- and diglycerides and mixtures of two or more thereof.

11. The ophthalmic composition according to claim 1, wherein the surfactant is selected from the group consisting of a polyethylene glycol sorbitan fatty acid ester, a sorbitan fatty acid ester, a polyethylene glycol fatty acid ester, a polyethylene glycol stearate ester, a polyoxyethylene glycol-block-polypropylene glycol-block-polyoxyethylene glycol-block, a polyethylene glycol lauryl ester and mixtures of two or more thereof.

12. The ophthalmic composition according to claim 1, wherein the composition is in the form of a gel for application to the eye.

13. The ophthalmic composition according to claim 1, wherein the mean diameter of the droplets of aphrons are from 0.5 to 50 µm.

14. A device for dropwise dispensing of a composition, wherein the device comprises a container holding the composition as defined in claim 1.

15. An ophthalmic composition comprising:

a polyaphron dispersion comprising cyclosporine, less than 15% of a hydrophobic discontinuous phase by weight of the composition; and a hydrophilic continuous phase comprising less than 0.5% of surfactant by weight of the ophthalmic composition;

wherein the surfactant comprises a non-ionic non-halogenated surfactant, wherein the ophthalmic composition does not comprise a fluorinated surfactant, the ophthalmic composition is a sterile and/or aseptic composition in the form of an eye drop formulated for administration to an eye, and wherein the polyaphron dispersion remains intact under shear stress caused by blinking of a patient's eyelid when the composition is in place in the patient's eye.

* * * * *